(12) United States Patent
Ebensen et al.

(10) Patent No.: US 8,053,417 B2
(45) Date of Patent: Nov. 8, 2011

(54) HEXOSYLCERAMIDES AS ADJUVANTS AND THEIR USES IN PHARMACEUTICAL COMPOSITIONS

(75) Inventors: Thomas Ebensen, Hannover (DE); Michael Morr, Wolfenbuettel (DE); Carlos Guzman, Wolfenbuettel (DE)

(73) Assignee: Helmholtz-Zentrum fuer Infektionsforschung GmbH, Vraunschweig (DE)

( * ) Notice: Subject to any disclaimer, the term of this patent is extended or adjusted under 35 U.S.C. 154(b) by 876 days.

(21) Appl. No.: 12/090,279

(22) PCT Filed: Oct. 19, 2006

(86) PCT No.: PCT/EP2006/010086
§ 371 (c)(1),
(2), (4) Date: Apr. 15, 2008

(87) PCT Pub. No.: WO2007/045469
PCT Pub. Date: Apr. 26, 2007

(65) Prior Publication Data
US 2008/0206319 A1    Aug. 28, 2008

(30) Foreign Application Priority Data
Oct. 19, 2005 (EP) .................................... 05022771

(51) Int. Cl.
*A61K 31/70* (2006.01)
*A61K 31/7028* (2006.01)
*C07H 15/04* (2006.01)

(52) U.S. Cl. ............. 514/25; 514/23; 536/17.9; 536/4.1

(58) Field of Classification Search .................... 514/25, 514/23; 536/17.9, 4.1
See application file for complete search history.

(56) References Cited

FOREIGN PATENT DOCUMENTS

| EP | 0510356 A1 | 3/1992 |
|----|----|----|
| WO | WO 99/52549 | 10/1999 |
| WO | WO 03009812 | 2/2003 |
| WO | WO 2004/009125 A2 | 7/2003 |
| WO | WO 2004 028475 | 4/2004 |
| WO | WO 2006/027685 A2 | 9/2005 |

OTHER PUBLICATIONS

Vajdy et al. Mucosal Adjuvants and Delivery System for Protein, DNA, and RNA-based Vaccines, Immunology and cell Biology (2004) 82, pp. 617-627.
Singh et al. Advances in Vaccine Adjuvants, 1999 Nature Amarica Inc., pp. 1077-1081.

*Primary Examiner* — Shaojia Anna Jiang
*Assistant Examiner* — Michael C Henry
(74) *Attorney, Agent, or Firm* — Whitham Curtis Christofferson & Cook, PC

(57) ABSTRACT

The present invention relates to new adjuvants and the uses in pharmaceutical compositions, like in vaccines. In particular, the present invention provides new compounds useful as adjuvants for prophylactic and/or therapeutic vaccination in the treatment of infectious diseases, inflammatory diseases, autoimmune diseases, tumours, allergies as well as for the control of fertility in human or animal populations. The compounds are particularly useful not only as systemic, but preferably as mucosal adjuvants. In addition, the invention relates to its uses as active ingredients in pharmaceutical compositions.

27 Claims, 12 Drawing Sheets

* with respect to ß-Gal (p<0.001)

with respect to ß-Gal + αGalCer (p<0.001)

HEXOSYLCERAMIDES AS ADJUVANTS AND THEIR USES IN PHARMACEUTICAL COMPOSITIONS

FIELD OF THE PRESENT INVENTION

The present invention relates to new adjuvants and the uses in pharmaceutical compositions, like in vaccines. In particular, the present invention provides new compounds useful as adjuvants for prophylactic and/or therapeutic vaccination in the treatment of infectious diseases, inflammatory diseases, autoimmune diseases, tumours, allergies as well as for the control of fertility in human or animal populations. The compounds are particularly useful not only as systemic, but preferably as mucosal adjuvants. In addition, the invention relates to its uses as active ingredients in pharmaceutical compositions.

BACKGROUND OF THE INVENTION

Infectious diseases are the major cause of morbidity and mortality, accounting for a third of the deaths which occur in the world each year. In addition, infectious agents are directly responsible for at least 15% of new cancers, and they also seem to be involved in the pathophysiology of several chronic diseases (e.g. inflammatory, vascular and degenerative diseases). Traditional infectious diseases are also highly expensive in terms of health-associated costs of infected patients and loss in productivity at work.

The main strategies used to prevent infectious diseases are therapy and prophylaxis. Vaccination has become the most cost-effective measure to prevent infections. However, there are still many diseases for which vaccines are not yet available or the available vaccines are not completely satisfactory due to low efficacy, high reactogenicity, poor stability and/or high costs. Thus, there is still an urgent need for both new and improved vaccines.

Despite the fact that vaccines have traditionally been used for the prophylaxis of infectious diseases, recent findings suggest that they are also a powerful tool for the immuno-therapy of transmissible diseases (e.g. viral hepatitis, *Helicobacter pylori* infections, herpes virus infections, etc.). In addition, vaccines can be used for the immune-therapy or immune-prophylaxis of autoimmune diseases, inflammatory diseases, tumours, allergies and for the control of fertility in human and/or animal populations. In particular, the last application seems to require the elicitation of efficient mucosal responses at the level of the reproductive tract.

Most infectious diseases are either restricted to the mucosal membranes or the etiologic agents need to transit the mucosa during the early steps of the infection. Therefore, it is desirable to obtain not only a systemic, but also a local mucosal immune response as a result of vaccination, thereby blocking both infection (i.e. colonization) and disease development. This may result in a more efficient protection against infection, facilitating also the eradication of diseases for which humans are the only reservoirs (i.e. blocking transmission to susceptible hosts). Parenterally-administered vaccines mainly stimulate systemic responses, whereas vaccines administered by a mucosal route mimic the immune response elicited by natural infections and can lead to efficient mucosal and systemic responses. Due to the apparent compartmentalization of the systemic and mucosal immune system, parenterally administered vaccines are less effective in protecting against mucosal pathogens (McGhee, J. R., Mestecky, J., Dertzbaugh, M. T., Eldridge, J. H., Hirasawa, M. and Kiyono, H. (1992) The mucosal immune system: from fundamental concepts to vaccine development. Vaccine 10, 75-88). Thus, administration of immunogens through the mucosal route is required to achieve full protection. However, most of the available vaccines are administered through the parenteral route, thereby eliciting a systemic immunity in the individual.

The administration of vaccines via the mucosal route offers several advantages over parenteral vaccination. These advantages include an ease of administration, the possibility of self-administration (e.g. by intranasal, rectal or oral application), the elimination of the chance of unwanted cross-infection due to the use of infected needles or non-sterile working, lower rates of side effects, higher acceptance by the public, better compliance of vaccination protocols (i.e. increment in the overall efficacy), simpler administration logistics and lower delivery costs, being particularly suitable for mass immunization programmes. However, the compartmentalisation at the level of the mucosal immune system has to be taken into consideration. In fact, immune responses which can be observed following intra-nasal vaccination may not necessarily occur after oral or intra-rectal immunisation. For example, oral vaccination may not stimulate efficient responses in the genitourinary and/or respiratory tracts.

Unfortunately, the delivery of antigens by the mucosal route is associated with a major problem, namely that antigens delivered by this route are generally poorly immunogenic. This is the result of different mechanisms, such as (i) accelerated antigen elimination by the non specific host clearance mechanisms (e.g. ciliar activity, peristaltism), (ii) antigen degradation by local enzymes, (iii) antigen alteration and/or structural modification as a result of extreme pH (e.g. acidic in the stomach, alkaline in the intestine), (iv) poor antigen penetration through the mucosa, (v) limited access of vaccine antigens to antigen presenting cells, and (vi) local peripheral tolerance.

To overcome these problems, different strategies have been used, such as antigen entrapment or association with physical or biological particles (e.g. microparticles, nanoparticles, bacterial ghosts), the use of virosomes or viral-like-particles, the use of liposomes or ISCOMS, the use of transgenic plants, antigen production by attenuated viral or bacterial carriers acting either as conventional vectors or as carriers for nucleic acid vaccines and/or their administration with mucosal adjuvants. However, despite the heavy body of experimental evidence generated in pre-clinical studies during the last years, almost no candidates have been transferred to the vaccine development pipeline.

The use of optimal adjuvants plays a crucial role in vaccination. Antigens administered without adjuvant only rarely mediate an adequate immune response. In addition, not only the strength but also the quality of the elicited immune response matters. Stimulation of an incorrect immunization pattern may lead to immunopathological reactions and exacerbation of the symptoms of infection. In this context, the adjuvant can help to assist the desired immune response. In other words, an adjuvant can modulate the immune response or redirect the immune response to balance the immune response in the desired direction.

Substances referred to as "adjuvants" are those which are added and/or co-formulated in an immunization to the actual antigen (i.e. the substance which provokes the desired immune response) in order to enhance the humoral and/or cell-mediated immune response ("Lexikon der Biochemie und Molekularbiologie", 1. Band, Spektrum, Akademischer Verlag 1995). That is, adjuvants are compounds having immunopotentiating properties, in particular, when co-administered with antigens. The use of many adjuvants is based solely on experience, and the effect can neither be accurately explained nor predicted. The following groups of adjuvants are traditionally used in particular: aluminum hydroxide, emulsions of mineral oils, saponins, detergents, silicon compounds, thiourea, endotoxins of gram-negative bacteria, exotoxins of gram-positive bacteria, killed or attenuated living bacteria or parts thereof.

An overview over the presently known mucosal adjuvants and delivery systems, e.g. the above mentioned particles, ICOMS, liposomes and viral-like particles, for protein, DNA- and RNA-based vaccines is given in Vajdy et al., Immunol. Cell Biol., 2004, 82, 617-627. Therein the currently available approaches in immunopentiation of mucosal vaccines are discussed.

That is, various mucosal adjuvants have been described which should serve as an alternative for the adjuvants useful for systemic administration, e.g. see Vajdy et al., supra. These mucosal adjuvants include heat labile enterotoxin and detoxified mutants thereof. In particular, genetically detoxified mutants of heat labile enterotoxin of *E. coli* have been developed as useful mucosal adjuvants. Moreover, cholera toxin of *vibrio cholera* is known as an adjuvant useful for mucosal vaccination. Further, the application of unmethylated CpG dinucleotides has been described. It was shown that CpG can bias the immune response towards a Th1 response and can modulate pre-existing immune responses. Saponins are also described as immunomodulatory substances, predominantly via the induction of specific cytokines which then modulate and/or activate the immune response.

In addition, as adjuvants which may be useful in mucosal vaccination the following have been described:

The MALP-2 molecule and Bisaxcyloxypropylcysteine-conjugates thereof, e.g. a Bispalmitoyloxypropylcysteine-PEG molecule is known to represent potent stimulants for macrophages. The usefulness of MALP-2 as an adjuvant was shown previously, see e.g. WO2004/009125 and WO2003/084568. In particular, it was demonstrated that MALP-2 can act as an effective mucosal adjuvant enhancing the mucosal immune response, e.g. fostering an enhanced expression of antigen-specific IgA antibodies.

Furthermore, it was shown that MALP-2 can activate dendritic cells and B-cells, both play an important rule in the induction of a specific humoral immune response. In addition preliminary studies demonstrate that a combination for biologically active HIV-1 tat protein and synthetic MALP-2 may be a promising vaccine with the MALP-2 component as an effective mucosal adjuvant.

Unfortunately, most of the compounds described above being useful as mucosal adjuvants are not utilisable due to their intrinsic toxicity, e.g. retrograde homing to neuronal tissues of bacterial toxoids and/or toxins at/in the derivatives after nasal vaccination.

Thus, none of these previously described mucosal adjuvants have been approved yet, but, today, only two systemic adjuvants received approval to be administered to humans and, hence, are used for the preparation of human vaccines. These adjuvants are Alum and MF59. However, both are not effective as mucosal adjuvants.

There has been an intensive search in recent years for novel adjuvants, including those for the mucosal administration route. Only a few substances have been found to be able to enhance mucosal responses. Among these, some act as carriers to which the antigens must be bound or fused thereto. Far fewer universally employable "true" adjuvants which are admixed to the antigens have been found, as outlined above.

Typically cell membranes are inter alia composed of lipids, like phospholipids. Roughly, phospholipids can be divided in phosphoglycerides and sphingolipids. The backbone of a sphingolipid is sphingosine. In all sphingolipids, the amino group of sphingosine is acylated to form a ceramide (N-acyl-sphingosine). The terminal hydroxyl group is also substituted. Thus, depending on the substituent a sphingomyelin, a cerebroside or a ganglioside is formed. In cerebrosides a glucose or galactose is linked to the terminal hydroxyl group of ceramide while in gangliosides an oligosaccharide is linked to the ceramide by a glucose residue.

Alpha-galactosylceramide (alpha-GalCer) as an example of alpha-hexosylceramide (alpha-HexCer) was originally isolated form the marine sponge Agelas mauritianus (Morita M., et al, J. Med. Chem., 1995, 38(12), 2176-2187). In particular, the compound Agelasphin-9b, (2S,3S,4R)-1-O-(alpha-D-galactopyranosyl)-16-methyl-2-[N—((R)-2-hydroxytetracosanoyl)-amino]-1,3,4-heptadecanetriol, is described as a potent antitumor agent. It is known that alpha-GalCer can enhance the protective immunity and displays immunomodulatory functions. Furthermore, it is described in the art that in vivo administration of alpha-GalCer leads to a potent activation of NKT-cells in mice, thus, initiating cytokine secretion, up-regulation of surface receptors and further activation of various cells of the innate and adaptive immune response. Additionally, it is speculated that alpha-GalCer has a therapeutic activity against tumors, infections and autoimmune diseases.

Alpha-galactosylceramide is able to bind to the CD1d molecule present in a subset of lymphocytes. Upon binding to CD1d, alpha-GalCer was demonstrated to activate murine and human NKT cells by recognition via antigen receptors expressed on said cells. Furthermore, it was demonstrated that nearly complete truncation of the alpha-GalCer acyl chain from 24 to 2 carbons does not significantly affect the mouse NKT cell response. Thus, the glycosyl moiety seems to be important for CD1d/GalCer and antigen receptor recognition and modification of said moiety is likely to influence binding and activation activity of alpha-GalCer.

Recently it has been described that glycosylceramides are useful as adjuvants for vaccines against infections and cancer, WO03/009812. In this document subcutaneous administration of alpha-galactosylceramides has been used to show enhancement and prolongation of malaria-specific T cell responses. Further, in WO2004/028475 the use of glycosylceramide analogues is shown. It is described that these analogues are able to immunomodulate the immune response, i.e. may activate or stimulate the immune response or, on the other hand, can have immunoinhibitory activity.

However, the use of alpha-GalCer or other glycosylceramides is limited in view of its stability and its tolerance towards the individual. Furthermore, the solubility of alpha-GalCer in aqueous solvents is poor and degradation due to enzymatic cleavage rapidly occurs. In addition, excretion of these compounds is rapid and, thus, higher dosage of said compounds is necessary.

PEGylation (i.e. the attachment of polyethylene glycol to proteins and drugs) is an upcoming methodology for drug development and it has the potential to revolutionise medicine by drastically improving the pharmacokinetic and pharmacodynamic properties of the administered drug [Parveen S, Sahoo S K. Clin Pharmacokinet 2006; 45(10):965-88.]. Since several years polyethylenglycole [is already used as a non-absorbable marker [Isenberg J I, Hogan D L, Koss M A, Selling J A. H, Gastroenterology 1986; 91(2):370-8], for the control of passive mucosal permeability (evaluated with a low-molecular-weight substance PEG 200) [Ventura U, Ceriani T, Moggio R., Scand J Gastroenterol Suppl 1984; 92:55-8] or as molecular weight marker (i.e., PEG 4000, FITCdextran 10.000). It was demostrated, that PEG showed only low intranasal irritation in humans [EP 0532546] and also low toxicity was found in rabbits or in sheeps after 1 repeated nasal application (three times a day) of pure PEG. The usage of pegylated immuno-nanoparticles synthesized with bifunctional PEG derivatives showed that these component can link the nanoparticle with the targeting MAb [Olivier J C, Huertas R, Lee H J, Calon F, Pardridge W M., Pharm Res 2002; 19(8):1137-43].

However, the use of pegylated compounds, such as the current standard therapy for HCV, pegylated interferon alpha in combination with ribavirin, has its limitations. Limited efficacy in patients with hepatitis C virus genotype 1 and the side effect profile will necessitate the development of new therapeutic approaches [Manns M P, Wedemeyer H, Cornberg M, Gut, 2006; 55(9), 1350-9]. Furthermore, the conjugation of an immunomodulator with PEG does not matter, that the pegylated compound still is able to act as an adjuvant. Studies with pegylated Malp-2 derivatives showed a decrease in cellular proliferation and also in the secretion of antigen-specific IgG titer in comparison to Malp-2. Until now, it has not been demonstrated, that a pegylated derivative of a chemical active compound was able to stimulate and activate an antigen-specific immune response via intranasal administration route. The usage of the conjugates according to the present invention, e.g. the new αGalCerMPEG compound as systemic, but also as mucosal adjuvant showed that said conjugates are able to enhance antigen specific immune responses without adverse side effects.

Hence, there is still a need in the prior art to provide new compounds useful as adjuvants, particularly as mucosal adjuvants and/or as vaccines overcoming the drawbacks mentioned above, in particular, having good stability and tolerance in the individual while being soluble in aqueous solvents, being protected against degradation in the individual and with good shelf life. In particular, there is a need for mucosal adjuvants which can elicit a strong immune response which represent a balanced or adjusted immune response involving both humoral and cellular components, thus, allowing effective prophylaxis or treatment of various diseases and conditions, specifically of infectious diseases or cancer.

Thus, the object of the present invention is the provision of mucosal adjuvants which can elicit and/or enhance and/or modulate (pre-existing) immune response in an individual or subject. In particular, the invention was based on the object of developing a range of novel, highly active adjuvants, particularly mucosal adjuvants which are non-toxic for humans and which can be employed with a wide variety of active ingredients to be assisted in conventional or novel vaccines such as, in particular, prophylactic or therapeutic vaccines, including cancer and DNA vaccines.

DESCRIPTION OF THE INVENTION

This technical problem is solved by the provision of the embodiments as characterized in the claims.

The present invention is generally concerned with the provision of new conjugates as depicted in formula (I) or salts or solvates thereof, useful as adjuvants, preferably as mucosal adjuvants. Furthermore, the present invention relates to new pharmaceuticals comprising at least one of the conjugates according to formula (I) as described herein with pharmaceutically acceptable carrier(s), optionally together with additional active ingredients.

That is, the present invention relates to the provision of the use of specific conjugates useful as adjuvants in therapeutic or prophylactic vaccination. Said conjugates are useful as systemic and are particularly useful as mucosal adjuvants being applied via the mucosa of the individual.

As used herein, the term "adjuvant" means substances which are added and/or co-formulated in an immunization to the active antigen, i.e. the substance which provokes the desired immune response, in order to enhance or elicit or modulate the humoral and/or cell-mediated (cellular) immune response against the active antigen. Preferably, the adjuvant according to the present invention is also able to enhance or to elicit the innate immune response.

The term "therapy" or "treatment" refers to a process that is intended to produce a beneficial change in the condition of an individual like a mammal, e.g., a human, often referred to as a patient, or animal. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy usually encompasses the administration of a drug, among others.

As used herein, the term "delivery system" refers to a system that is more inert and has less immunomodulatory effects than adjuvants and which can protect and deliver the vaccine to the site of interest through the site of administration. In particular, the delivery system allows for more efficient presentation of the antigen to the immune system. Examples of delivery systems are virus or virus-like particle, ISCOM, nanoparticles, microparticles, liposomes, virosomes and virus-like particles.

As used herein, the term "pegylated" refers to the conjugation of a compound moiety with conjugate moiety(ies) containing at least one polyalkylene unit. In particular, the term pegylated refers to the conjugation of the compound moiety with a conjugate moiety having at least one polyethylene glycol unit.

As used herein, the term "mucosal" refers to mucosal surface from the body such as the nasal, oral, gastro-enteric, rectal, urinary, conjunctial, glandular, e.g. mammary gland, epithelial mucous.

As used herein, the term "conjugate" refers to compounds comprising a conjugate moiety and a compound moiety. The term "conjugate moiety" refers to substituent $R_4$ of the general formula (I). The conjugate moiety aims to increase the applicability of the residual compound. In contrast, the term "compound according to formula (I)" or "compound moiety" refers to a compound of the general formula (I) without substituent B.

As used herein, the term "antigenic structure" or "antigen" refers to a structure capable of causing a cellular or humoral immune response. The antigenic structure, also known as epitope is the part of the antigen, which is presented by the MHC or MHC like molecules. Further, the epitope or antigenic structure represents the part of an antigen recognized by antibodies directed against said antigen.

As used herein, the term "modulate an immune response" refers to any change of the present state of the immune response. The immune response may be modulated insofar that the response is elicited or a pre-existing immune response is enhanced which may include decreasing specific aspects of the immune response, e.g. the immune response may be modulated by shifting the immune response from a more humoral to a more cellular immune response or vice versa. Further, the immune response may be modulated by switching or redirecting the response from a Th1 to Th2 or Th3 response or vice versa. In addition, the modulation of the immune response may encompass the activation or enhancement of the innate immune response.

As used herein, the term "individual" or "subject" which is used herein interchangeably refers to an individual or a subject in need of a therapy or prophylaxis. Preferably, the subject or individual is a vertebrate, even more preferred a mammal, particularly preferred a human.

As used herein, the term "carrier" refers to a diluent, adjuvant, excipient, or vehicle.

Thus, according to the first embodiment, the present invention relates to an alpha-Hexosylceramide (alpha-HexCer) conjugate according to formula (I)

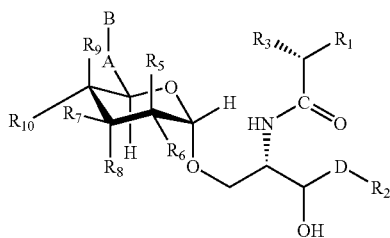

wherein
A is $CH_2$ or CO;
B represents $R_4$, $OR_4$, $NHR_4$, $PO_3R_4$, or $SO_3R_4$;
where $R_4$ is a conjugate moiety, which is a water-soluble and physiologically tolerated polymer;
$R_1$ and $R_2$ can be identical or different and are independently a linear or branched $C_{10}$-$C_{30}$ alkyl- and/or alkenyl-group;
D represents $CH_2$ or CH(OH);
$R_3$ represents H or OH;
$R_5$ and $R_6$ are substituents where either $R_5$ represents hydrogen and $R_6$ represents hydrogen, OH, $OC_1$-$C_6$ alkyl, $NH_2$, $NHCOC_1$-$C_6$ alkyl or $R_6$ is hydrogen and $R_5$ represents hydrogen, OH, $OC_1$-$C_6$ alkyl, $NH_2$, $NHCOC_1$-$C_6$ alkyl;
$R_7$ and $R_8$ are substituents where either $R_7$ represents hydrogen and $R_8$ represents hydrogen, OH, $OC_1$-$C_6$ alkyl, $NH_2$, $NHCOC_1$-$C_6$ alkyl or $R_8$ is hydrogen and $R_7$ represents hydrogen, OH, $OC_1$-$C_6$ alkyl, $NH_2$, $NHCOC_1$-$C_6$ alkyl;
$R_9$ and $R_{10}$ are substituents where either $R_9$ represents hydrogen and $R_{10}$ represents hydrogen, OH, $OC_1$-$C_6$ alkyl, $NH_2$, $NHCOC_1$-$C_6$ alkyl or $R_{10}$ is hydrogen and $R_9$ represents hydrogen, OH, $OC_1$-$C_6$ alkyl, $NH_2$, $NHCOC_1$-$C_6$alkyl; or salts or solvates thereof.

Preferably, in formula (I) $R_5$, $R_8$ and $R_{10}$ are each a hydrogen and $R_6$ is preferably hydrogen, OH, $OC_1$-$C_6$ alkyl, $NH_2$, $NHCOC_1$-$C_6$ alkyl, $R_7$ and $R_9$ each are OH, $OC_1$-$C_6$ alkyl. Particular preferably, $R_5$, $R_8$ and $R_{10}$ are hydrogen and $R_6$, $R_7$ and $R_9$ are hydroxyl groups.

$R_1$ and $R_2$ may be identical or may be different and are independently an alkyl group or alkenyl group having $C_9$ to $C_{29}$ residues. Preferably, $R_1$ is $C_{19}$ to $C_{29}$, particularly $C_{24}$, and $R_2$ is $C_{10}$ to $C_{20}$, particularly $C_{14}$.

As a conjugate of formula (I), particularly preferred are conjugates of alpha-galactosylceramides, i.e. wherein $R_5$, $R_8$ and $R_{10}$ are a hydrogen atom and $R_6$, $R_7$ and $R_9$ are a hydroxyl group, like (2S,3S,4R)-1-(alpha-D-galactopyranosyloxy)-2-hexacosanoylamino-3,4-octadecanediol. Preferably are conjugates of this galactosylceramides wherein said conjugate has at least one polyethylene glycol unit.

The conjugate moiety of the conjugate according to the present invention is a covalently bonded, physiologically tolerated conjugate moiety, which is suitable for converting the hexosylceramide into a more water-soluble form. The conjugate moiety is a water soluble polymer, e.g. a dextran, a sugar, a polyvinylpyrrolidone, an alginate, a pectin or collagen. The conjugate moiety is characterized in that is provides good water and is not immunogenic.

The conjugate moiety of the hexosylceramide conjugate claimed herein, is in a preferred embodiment, a conjugate moiety containing at least one polyalkylene glycol unit of the formula:

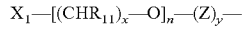

where
$X_1$ is hydrogen or a hydrocarbon which may contain heteroatom(s), e.g. C1 to C6 alkoxy group;
Z is a divalent linkage group, such as C=O or $CHR_{11}$;
$R_{11}$ is independently any one of hydrogen, OH, $OR_{12}$ or CO—$R_{13}$;
$R_{12}$ is independently any one of hydrogen or $C_1$-$C_6$ alkyl group;
$R_{13}$ is independently any one of hydrogen, OH, $OR_{12}$ or $NR_{14}R_{15}$;
$R_{14}$ and $R_{15}$ are independently any one of hydrogen or hydrocarbon which may contain heteroatom(s) and which may form a ring;
n is an integer of 1 to 100;
x is independently an integer of 1 to 10;
y is an integer of 0 to 10.
Preferably, n is an integer of 2 to 50, like 2 to 10, in particular 3 to 5.
x is preferably an integer of 2, 3 or 4, in particular 2.
y is preferred an integer of 1 to 5, in particular, 1 to 3, in another preferred embodiment, y is 0.
$X_1$ is preferentially $OR_{16}$, $N(R_{16})_2$, $SR_{16}$ or $COOR_{16}$, wherein each $R_{16}$ is individually hydrogen, benzyl or $C_1$-$C_6$ alkyl group, preferably a $C_1$-$C_6$ alkoxy group, like a methoxy, ethoxy or propoxy group.
$R_{11}$ is preferably a hydrogen atom.

Thus, the polyalkylene glycol unit mentioned above may preferably contain subunits —$[(CHR_{11})_x$—$O]_n$ of ethylene glycol, propylene glycol or butylene glycol or combinations thereof. The chain length of each of the polyalkylene glycol units may be in the range of 1 to 100 subunits, preferably, 2 to 50 subunits, like 2 to 10 subunits, particularly in the range of 3 to 5 subunits.

Particularly preferred is $R_4$ a methoxypolyalkyleneglycol-carbonyl-residue wherein the alkylene moiety is an ethylene or propylene moiety.

Hence, preferably the conjugates are in a pegylated form to increase the solubility in hydrophilic solvents and hydrophilic environment. Furthermore, the conjugate moiety allows protecting the compound moiety, i.e. the active mucosal adjuvant moiety, against enzymatic degradation, structural modification due to change of the pH, mechanical removal, etc. Thus, primarily the stability of the compound is increased. Another beneficial effect of conjugation is to increase the retention time in the individual, e.g. to delay the renal excretion, while being well-tolerated, e.g. being non immunogenic, by said organism.

Surprisingly, the conjugate maintains its CD1d binding activity while showing improved stability and higher activity. The data demonstrate that even 10-fold lower concentration of the active moiety, namely the alpha-HexCer moiety, of conjugates maintain their stimulatory activities compared to the pure alpha-HexCer compound. Furthermore, the water-solubility of the alpha-HexCer compound is improved. In addition, as shown in the examples, the conjugate according to the present invention, like the alphaGalCerMPEG which is a conjugate wherein a methyl-PEG-CO residue is bound the substituent $R_4$, exerts stronger adjuvant properties than the parental compound alphaGalCer being a superior inducer of sIgA and Th2 responses both at local and remote mucosal effector sites.

Lastly, the shelf-life of the alpha-HexCer compound was increased after conjugation with the water-soluble polymer. That is, the stimulatory capacities of alphGalCerMPEG on immune cells were maintained intact for at least two months after incubation of a stock solution (10 µg/ml in sterile water/Ampuwa) at either 4° C. or 25° C.

Specifically, the conjugate moiety comprises at least two chains having polyalkylene glycol units. That is, the conjugate may be a branched compound wherein each arm contains a polyalkylene glycol unit. Particularly preferred are conjugate moieties wherein the polyalkylene glycol unit is a polyethylene, polypropylene or polybutylene glycol unit.

In a particularly preferred embodiment, the conjugate moiety being a branched moiety wherein at least two arms containing polyethylene glycol units having 3 to 5 ethylene glycol subunits and a methoxy group at the free end of the polyethylene group. In particular, the branched moiety comprises 4 or 6 arms each having 3 ethylene glycol subunits and a methoxy group at the free end of the polyethylene group.

In particular, the alpha-HexCer conjugate is characterized in that the conjugate $R_4$ is 4armPEG((S)-10-Amino-6,9,13,16-tetraoxo-N,N',8,14-tetrakis(3,6,9,12-tetraoxamidec-1-yl)-5,8,14,17-tetraazahenicosane-1,2'-diamide), 6armPEG or 8armPEG, see also http://ww.celares.com. Other suitable conjugate moiety comprising at least one polyethylene unit are obtainable e.g. from celares GmbH, Berlin, see http://www.celares.com.

The conjugates of formula (I) may be in the form of pharmaceutically acceptable non-toxic salts thereof. Salts of the conjugates of formula (I) include acid added salts, such as salts with inorganic acids (e.g. hydrochloric acid, sulphuric acid, nitric acid and phosphoric acid) or with organic acids (e.g. acetic acid, propionic acid, maleic acid, olec acid, palmitic acid, citric acid, succinic acid, tartaric acid, fumaric acid, glutamic acid, panthothenic acid, laurylsulfonic acid, methanesulfonic acid and phthalic acid).

The conjugates of formula (I) may be in the form of solvates thereof (e.g., hydrates).

The present invention is not limited to the alpha-Hexosylceramides conjugates and compounds but also encompasses the beta-Hexosylceramide conjugates and compounds as well as the salts or solvates thereof.

The synthesis of conjugates may be conducted by methods known to the person in the art. For example, a hydroxyl group may be converted into a halogen residue, e.g. Cl. Br, I and this residue can react with modified conjugates having a free amino-group. For example, synthesis of pegylated conjugates is described in Veronese F. M., Biomaterials 22 (2001), 405-417 and Kodera Y., et al., Prog. Polym. Sci. (1998), 23, 1233-1271 which are incorporated herein by reference.

In addition, the synthesis of alpha-glycosylceramides and alpha-galactosylceramides are described generally in e.g. WO93/05055, WO94/02168, WO94/06020, WO94/24142 and Morita M., et al., Bioorganic & Medical Chemistry Letters, 1995, 5(7), 699-704 which are all incorporated herein by reference.

In a preferred embodiment, the conjugate(s) according to formula (I) or salts or solvates thereof are useful as mucosal adjuvant(s), in particular, for intranasal, intra NALT, oral, intra-rectal, conjunctival, intra-vaginal, intrathecal, intra-bronchial, intrapulmonary, or intra-urethral administration, administration into the milk ducts of the breast or by inhalation.

Particularly preferred is the intranasal administration or the administration by inhalation using suitable aerosol formulations. Aerosol formulations useful for administration of vaccines are known in the art.

The conjugates according to formula (I) or salts or solvates thereof are also suitable as systemic adjuvant(s). Thus, the adjuvants described herein are also applicable as parenteral adjuvant(s), in particular, in subcutaneous, intravenous, intradermal, topical or intramuscular administration.

The adjuvant of the invention can be linked by all methods known to the skilled person to the antigen or active molecule intended for the vaccination, be incorporated together with the latter in physical (e.g. microparticles, nanoparticles, liposomes, ISCOMS, polymers) or biological particles (bacteria, bacterial parts) or virosomes or be mixed with the antigen. For binding to carriers it is also possible to provide transport molecules or transport proteins as carriers.

The conjugate(s) according to the formula (I) or salts or solvates thereof is/are preferably present in a preparation with the active vaccination component (e.g. the antigen) which is suitable and provided for intranasal, intra-NALT (nasal associated lymphoid tissue), aerosolized, oral, intrarectal, conjunctival, intravaginal, intraurethral administration or for administration into the milk ducts of the breast. Particularly, the preparation is provided in formulation suitable to be taken up via the respiratory tract or the gastro-intestinal tract. Alternatively, the mucosal adjuvant of the invention can be present in a kit for co-administration with a vaccine by one of the aforementioned routes and be adapted therefore where appropriate. That is the vaccine may be administered simultaneously, sequentially or separately with the active vaccination component.

In another embodiment, the present invention relates to methods of treating individuals afflicted with a disease or condition that can be treated by modulating the immune response comprising administering to said individual an effective amount of a pharmaceutical comprising the conjugates according to formula (I), salts and solvates thereof as defined herein as an adjuvant, particularly as a mucosal adjuvants together with an active vaccination component, and, optionally, a pharmaceutically acceptable carrier.

Preferably, the method relates to the treatment of individuals afflicted with an infectious disease wherein the infectious disease is produced by an infectious agent selected among those causing human or animal disease at the level of the respiratory tract, gastrointestinal tract, genitourinary tract, osteoarticular system, skin or mucosa.

The conjugates or salts or solvates thereof as defined herein are particular useful as mucosal adjuvants for activating or enhancing in vitro and/or in vivo the antigen presenting function of antigen presenting cells for a therapeutic or prophylactic intervention. That means, the adjuvants can stimulate macrophages, can stimulate or enhance the humoral immune response, e.g. enhancing or stimulating the production of antibodies. In addition, the adjuvants can also enhance or stimulate the cellular immune response, e.g. increasing the proliferation of T-cells. Further the conjugates of formula (I) can not only activate or stimulate components of the adaptive immune system but also of the innate immune system, like activating NK-cells or NKT-cells. In addition, it is possible to use the adjuvant(s) for ex vivo stimulation in cell culture, e.g. for the production of dendritic cells, etc. These cells obtained by ex vivo stimulation may be used for autologous cell transfer in transplantation or as a cell based vaccine against diseases or conditions, like the diseases and conditions mentioned above, including cancer, autoimmune disease or allergies.

Thus, in case of the use of the conjugates or salts or solvates thereof as defined herein as an adjuvant, the pharmaceutical composition according to the present invention is preferably a vaccine, comprising said compounds or conjugates or salts or solvates thereof as pharmaceutically acceptable adjuvant(s) together with the active vaccination component (e.g. the antigen) and, optionally, a pharmaceutically acceptable carrier, diluent, preservative, adjuvant other than the adjuvant according to the present invention, immunomodulator or excipient.

The active vaccination component may be any component suitable to elicit, enhance or modulate an immune response in an individual. The active vaccination component is suitable particularly for intranasal, intra-NALT, oral, intra-rectal, conjunctival, intra-vaginal, aerosolized or intra-urethral administration, or administration into the milk ducts of the breast.

For example, the active vaccination component, the active ingredient of the pharmaceutical composition, comprises at least one or more different antigens in the form of peptides, proteins, polysaccharides, glycolipids or DNA encoding them or bacterial ghost, virosomes, or attenuated vaccines.

Preferentially, the antigen(s) are tumor antigen(s) or antigen(s) derived from infectious agents. The infectious agents include those agents which normally enters individual's organism by crossing the mucous membrane.

The pharmaceutical composition comprising adjuvant(s) according to the present invention, an active vaccination component, optionally additional carrier, diluent, preservative, adjuvant other than the adjuvant according to the present invention, immunomodulator or excipient may additionally contains components, like compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

However, the conjugates according to formula (I), salts and solvates thereof as defined herein for the use as adjuvants may also be a component of a pharmaceutical composition provided in a formulation suitable for parenteral administration, in particular, in subcutaneous, intravenous, intradermal or intramuscular administration.

Further, the conjugates according to the present invention are useful in tumor therapy including the in vitro generation or in vitro priming of autologous cells for adoptive cell transfer in tumor therapy and transplantation. Moreover, the adjuvants are useful for the induction of cross-tolerance against microbial components, like endotoxins, to protect against septic shock or other severe forms of diseases induced by microbial components.

In addition, the conjugates themselves as defined herein may display a pharmaceutical activity, e.g. are to be useful in the prophylaxis and treatment of various diseases and conditions, like cancer, infectious diseases, septic shock, chronic and inflammatory processes, autoimmune diseases, allergies, etc.

Hence, the conjugates according to formula (I) or salts or solvates thereof are also useful for the preparation of a pharmaceutical to prevent or treat infectious diseases, septic shock, cancer, tumours, autoimmune diseases, allergies, or chronic or acute inflammatory processes.

The conjugates according to the present invention and salts or solvates thereof, particularly, the pegylated conjugates, can be used as active ingredients in pharmaceuticals useful for the prevention or treatment of infectious diseases, septic shock, tumours, autoimmune diseases, allergies, or chronic or acute inflammatory processes. In particular, the conjugates or salts or solvates thereof are contained in pharmaceuticals useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, *helicobacter pylori*, herpes virus, etc.; bacterial infections, such as tuberculosis, leprosy and listeriosis, and parasitic infections such as malaria.

Thus, in a further aspect, the present invention relates to pharmaceutical compositions comprising conjugates according to formula (I) or salts or solvates thereof, in particular, conjugates containing at least one conjugate moiety comprising a polyalkylene glycol unit, as defined herein or salts or solvates thereof and, optionally, a pharmaceutically acceptable carrier. Such pharmaceutical compositions comprise a therapeutically effective amount of the conjugates and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin (18$^{th}$ ed., Mack Publishing Co., Easton, Pa. (1990)). Such compositions will contain a therapeutically effective amount of the aforementioned conjuates according to formula (I), salts or solvates thereof, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve an increase in the immunological responses to infection or a suppression of the responses to inflammatory processes.

In vitro assays may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The term "administered" means administration of a therapeutically effective dose of the aforementioned pharmaceutical composition comprising the conjugates according to formula (I), salts and solvates thereof as defined herein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In still another embodiment, the present invention relates to methods of treating individuals suffering from infectious diseases, septic shock, tumours, autoimmune diseases, allergies, or chronic or acute inflammatory processes comprising the step of administering to said individual an effective amount of a pharmaceutical comprising a conjugate according to formula (I) or salts or solvates thereof as the active ingredient, and, optionally, a pharmaceutically acceptable carrier. In particular, the method is useful for preventing or treating cancer and/or tumours, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, *helicobacter pylori*, herpes virus, etc.; bacterial infections, such as tuberculosis, leprosy and listeriosis, and parasitic infections such as malaria.

Further, the pharmaceutical composition may contain additionally components, e.g. compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

In addition, the pharmaceutical composition described herein may be characterized in that the components of the pharmaceutical composition are associated and/or incorporated and/or coated to a physical particle, preferably microparticle, nanoparticle, liposome, ISCOM, copolymer and/or biological particle, preferably bacterial ghosts.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intraarterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 µg per kg body weight; however, doses below or above this exemplary range are envisioned, especially considering the aforementioned factors.

In still another aspect, the present invention relates to the use of the compound(s). or salts or solvates thereof as defined herein in a pharmaceutical preparation to control fertility in human or animal populations.

Finally, the present invention relates to kits comprising the hexosylceramide conjugate according to the present invention or salts or solvates thereof. In particular, the kit is useful for the preparation of pharmaceutical compositions. Optionally, the kit contains instructions for preparing the pharmaceutical composition.

In a preferred embodiment thereof, the kit contains the hexosylceramide compound or conjugate according to the present invention or salts or solvates thereof as an adjuvant and an antigen comprising an antigenic structure and, optionally, a pharmaceutically acceptable carrier, diluent, preservative, adjuvants other than the conjugates according to the present invention, immunomodulators or excipient and instructions for preparing a vaccine.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.tigr.org/, are known to the person skilled in the art and can also be obtained using, e.g., http://www-.google.de. An overview of patent information in biotechnology and a survey of relevant sources of patent information useful for retrospective searching and for current awareness is given in Berks, TIBTECH 12 (1994), 352-364.

BRIEF DESCRIPTION OF THE FIGURES

FIG. 1 shows a scheme for the synthesis of alphaGalCerMPEG according to the present invention.

FIG. 2 shows cytometric determination of various molecules including co-stimulatory molecules on the surface of murine dendritic cells after stimulation with alpha-GalCer, alphaGalCerMPEG and PEG alone.

FIG. 3 provides a comparison of β-Gal antigen-specific IgG antibody expression in serum of immunized animals. In (A) the results of intranasal (i.n.) administration is shown. (B) provides the serum levels of antigen specific IgG expression after parenteral administration. Shown is a comparison of mice immunized with β-gal alone, β-gal+alphaGalCer (10 μg/dose) and β-gal+alphaGalCerMPEG (1 μg/ml active moiety/dose)

FIG. 4 shows a comparison of β-Gal specific secretory IgA expression in the nose, lung and vagina of immunized animals.

FIGS. 5A and B illustrates the stimulation of spleen cells with various amounts of alphaGalCerMPEG and alpha-GalCer and at different time points after i.n. administration FIG. 5B).

FIG. 6 demonstrates that alpha GalCerMPEG is an efficient adjuvant for the stimulation of spleen cells in i.n. and s.c. vaccination.

FIG. 7 shows the expression of the IgG isotypes being specific for the antigen β-gal in mice after i.n. and s.c. administration of β-gal, β-gal/alpha-GalCer, and β-gal/alpha-GalCerMPEG, respectively.

FIG. 8 illustrates the expression and secretion of Th1 and Th2 cytokines of spleen cells after re-stimulation with the antigen β-gal after previous i.n. vaccination with β-gal alone, β-gal/alpha-GalCer, and β-gal/alpha-GalCerMPEG, respectively.

FIG. 9 illustrates the expression and secretion of Th1 and Th2 cytokines of spleen cells after re-stimulation with the antigen β-gal after previous s.c. vaccination with β-gal alone, β-gal/alpha-GalCer, and β-gal/alpha-GalCerMPEG, respectively.

FIGS. 10 A and B demonstrates the ability of spleen cells to secrete IFNγ and IL-4, respectively, after i.n. and s.c. vaccination with β-gal alone, β-gal/alpha-GalCer, and β-gal/alpha-GalCerMPEG, respectively.

FIG. 11 illustrates the in vitro stimulation of lytic activity by alphaGalCerMPEG. Spleen cells from mice injected with alphaGalCer (10 μg), alphaGalCerMPEG (10 μg) or CpG (100 Mg) were recovered after 48 h and used as effectors in a 51Cr-release assay with YAC-1 cell targets. The results are expressed as percentage of lysis and they are average of triplicates.

FIG. 12 demonstrates the effect of co-administration of alphaGalCerMPEG on CTL responses measured by the VITAL assay (in vivo CTL)

The present invention is further described by reference to the following non-limiting figures and examples.

EXAMPLES

Figure 1:
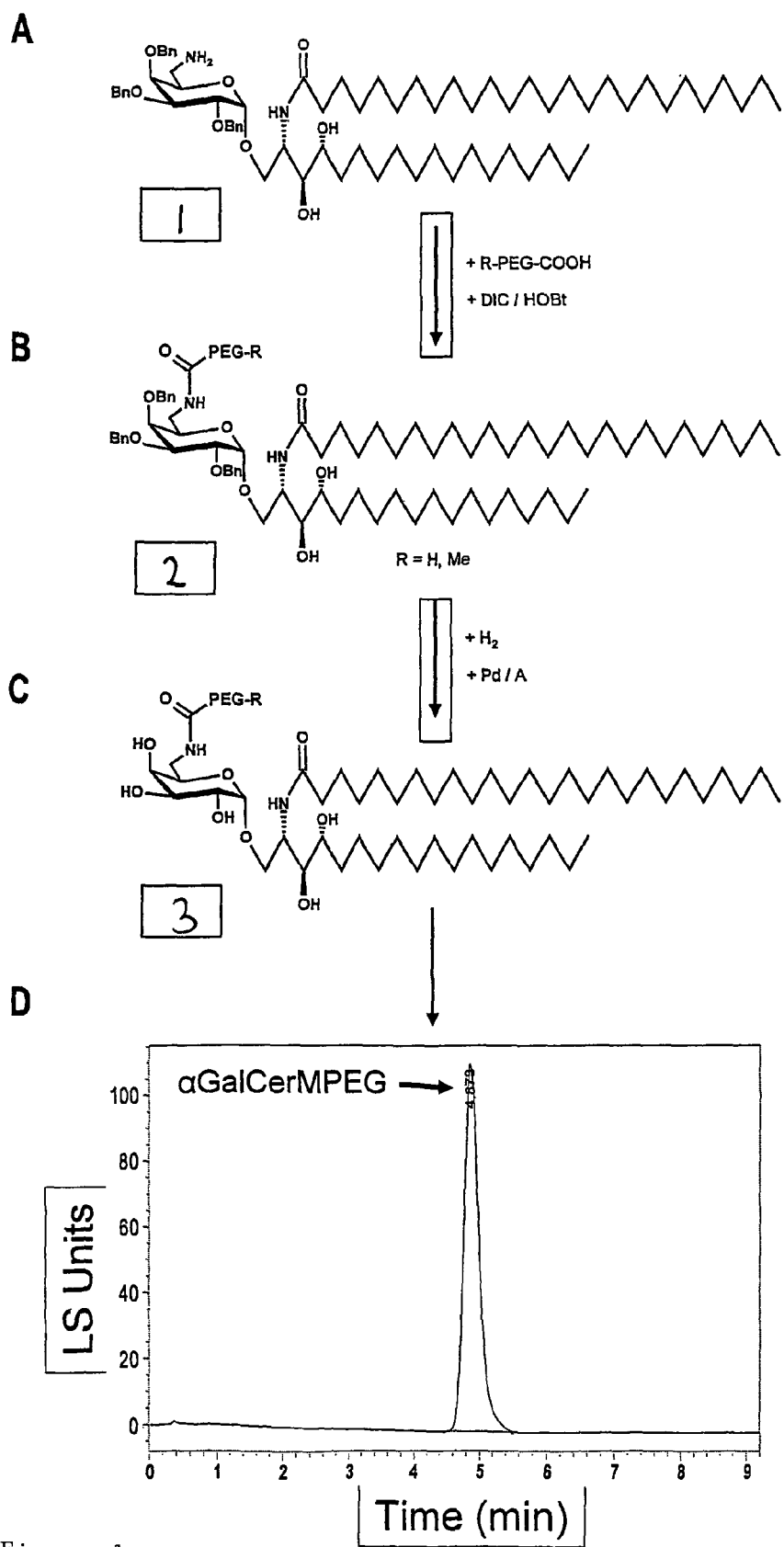
FIG. 1.

Abbreviations Used Herein alpha-GalCer: alpha-Galactosylceramide DIC—Diisopropylcarbodiimide
PEG: Polyethyleneglycol HexCer: hexosylceramide
DCM: Dichloromethane MPEG:
Methoxypolyethyleneglycol HOBt: Hydroxybenztriazol
BPPcysPEG: 2,3-Bis(palmitoyloxy)-propyl-L-cysteinyl-carboxypolyethylene glycol 1. Synthesis of Alpha-GalCer-MPEG The synthesis of the alpha-GalCer-MPEG according to the present invention is shown in FIG. 1. In brief, 150 mg (75 μMol) R-PEG-COOH (R=Methyl being abbreviated with M) were dissolved in 2 ml anhydrous DCM and 10.1 mg (75 μMol) Hydroxybenzotriazole (HOBt) and 12 μl (77 μMol) Diisopropylcarbodiimide (DIC) were added. After 30 min. 56.4 mg (50 μMol) of compound 1 shown in FIG. 1, e.g. synthesized by the method described in Zhou, X-T., et al. organic letters, 2002, 4(8), 1267-1270, in 5 ml anhydrous Dichloromethane (DCM) were added and reacted by stirring in the absence of humidity for about 15 h at room temperature. After concentration to dryness the residue was resolved in small amounts of chloroform and purified by means of silica gel chromatography (20×1.5 cm) using chloroform und chloroform/methanol (95:5) as eluents. After concentration the fraction containing the compound 2, about 150 mg of compound 2 as shown in FIG. 1 was obtained.

Cleavage of the O-benzene Protection Groups by Hydrogenation

About 150 mg of compound 2 obtained above was dissolved in 12 ml of a mixture of ethyl acetate/methanol (1:1) and was hydrogenated with hydrogen using 50 mg palladium/charcoal (10%) for about 9 h at 40° C. After separation of the catalyst and filtration using silica and washing with an admixture of the above mentioned solvents, the fraction was concentrated to dryness and about 120 mg of compound 3 of FIG. 1 was obtained. After purification by silica gel chromatography using a mixture of chloroform and methanol in ratios of 95:5/90:10/85:15 and 80:20, respectively, as the eluent, evaporation of the solvent and lyophilisation from water about 100 mg of compound 3 was obtained. The structure of the new water-soluble alpha-GalCerMPEG (compound 3) was proven by $^1$H und $^{13}$C-NMR and MALDI-MS-spectra (FIG. 1D).

2. In vitro Stimulation of Primary Bone Marrow-derived Murine Dendritic Cells with AlphaGalCer-MPEG Experimental protocol: primary bone marrow-derived dendritic cell cultures were obtained from BALB/c mice following in vitro maturation of precursors in the presence of recombinant GM-CSF ($5 \times 10^4$ U/ml), according to established protocols. Mature dendritic cells were stimulated with 10 ng/ml of E. coli lypopolysaccharide (LPS), 10 ng/ml of alpha-GalCer or alphaGalCerMPEG, after 12 h and 24 h, respectively, the stimulation of cells were analyzed by flow cytometry to assess the expression of surface markers which are relevant for their antigen presentation capacity.

In order to identify compounds which may have potential as adjuvants for in vivo applications in the field of vaccines, a first in vitro screening based on the use of primary cultures of bone marrow-derived dendritic cells was established. Dendritic cells were selected since they represent the most efficient antigen presenting cells and they play a key role in primary immune responses. In fact, they represent the only cell type able to activate resting T cells initiating primary immune responses in vivo. Thus, dendritic cell cultures were treated with the tested title compounds or LPS, which was used as a positive control. At different time intervals, samples were taken, stained with fluorescent-labeled antibodies specific for cellular markers critical for the antigen presenting capacities of dendritic cells, and analyzed by flow cytometry.

Figure 2:
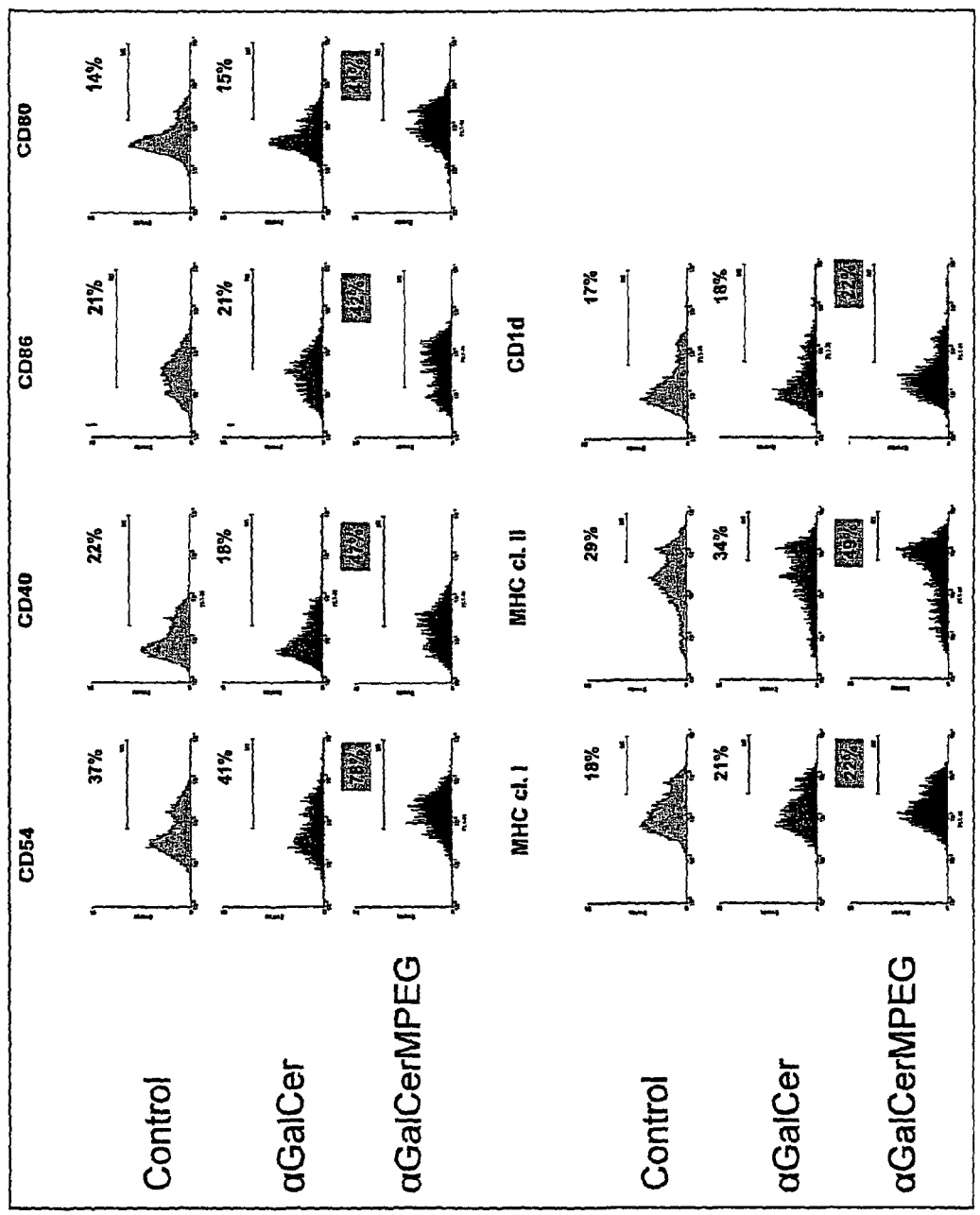
FIG. 2.

The obtained results (FIG. 2) demonstrated that in contrast to the control, group which received alpha-GalCer, the expression of CD40 and the co-stimulatory molecule CD86 and CD80 was up-regulated in the alphaGalCerMPEG treated dendritic cells. In addition, the expression of the CD1d molecule is increased after stimulation with alphaGalCerMPEG.

Co-stimulatory molecules deliver signals which, in addition to the presentation of the processed epitopes in the context of the MHC class II molecules, are essential for the efficient activation of T cells. It has been previously reported that the adjuvanticity of well-established mucosal adjuvants, such as cholera toxin, involves the selective up-regulation of the expression of co-stimulatory molecules. Thus, these in vitro results strongly argue for a high potential of alphaGalCerMPEG as mucosal adjuvants.

3. Intranasal and Subcutaneous Co-administration of AlphaGalCerMPEG with a Soluble Antigen Stimulates Efficient Systemic Humoral Responses Experimental protocol: six-eight weeks-old female BALB/c (H-2d) mice were purchased from Harlan Winkelmann GmbH (Borchen, Germany) and treated in accordance with local and European Community guidelines. Groups of 5 mice each were immunized on day 1, 14 and 28 with 30 μg of β-gal (Boehringer, Mannheim, Germany), alone or with 10 μg of alphaGalCerMPEG. For intranasal (i.n.) immunization, 10 μl were applied to each naris, whereas for the s.c. injection β-gal with or without alphaGalCerMPEG was resuspended in a volume of 20 μl PBS per animal. Serum samples were collected at day 38 after immunization and stored at −20° C. prior to determination of β-gal-specific antibodies. 96-well Nunc-Immuno MaxiSorp assay plates (Nunc, Roskilde, Denmark) were coated with 100 μl of β-gal (Boehringer, Mannheim, Germany) at 5 μg/ml in 0.05 M carbonate buffer (pH 9.6) per well. Serial two-fold dilutions of sera or lavages in PBS with 1% BSA and 0.05% Tween 20 were added (100 μl/well), and plates incubated for 16 h at 37° C. After washing, biotinylated γ-chain-specific goat anti-mouse IgG (Sigma Chemie, Deisenhofen, Germany) was added, and plates were incubated for an additional 1 h at 37° C. After four washes, 100 μl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. Endpoint titers were expressed as the reciprocal log 2 of the last dilution, which gave an optical density at 405 nm of 0.1 units above the values of the negative controls after 15 to 30 min of incubation.

In view of the above in vitro results, additional in vivo studies have been conducted. In detail, the immune responses using alphaGalCerMPEG as adjuvant applied by the two most effective routes, namely s.c. and i.n. were determined. Thus, the capacity of alphaGalCerMPEG to stimulate efficient humoral immune responses was evaluated, by determining the serum titers of β-gal-specific antibodies in vaccinated mice.

Figure 3A:
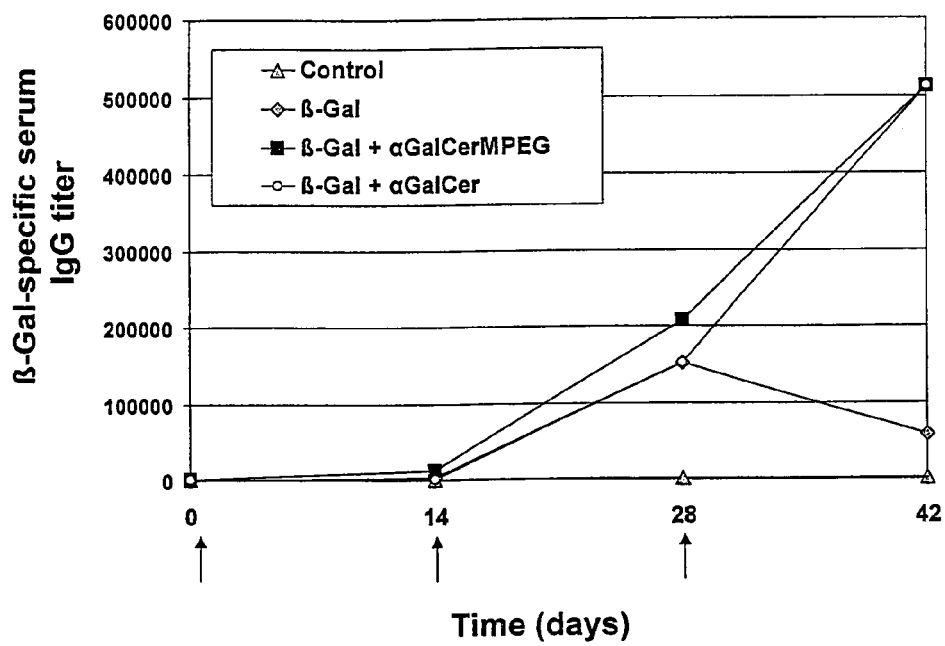
FIG. 3.

As shown in FIG. 3A, i.n. administration of β-gal alone (30 μg/dose) resulted in the induction of very low antibody titers, even after the second boost (day 28). In contrast, in the presence of alphaGalCerMPEG, i.n. administration of β-gal induced very high titers of specific IgG in all mice already after one dose, and by the end of the immunization protocol, titers were 32× fold higher than in animals vaccinated with 1-Gal alone. Vaccination by the parenteral route (FIG. 3B) results in IgG titers similar to vaccination using β-Gal alone. The kinetics and the overall efficacy of the antibody responses obtained using 5 to 10 μg of alphaGalCerMPEG per dose were similar to those observed by administering β-gal together with BPPcysPEG (O.5 μg boil active per animal), which is known to function well as a mucosal adjuvant. The reduction of the dosage to 1 μg per animal resulted in a decrease of the immune response in a dose dependent manner.

Figure 3B:
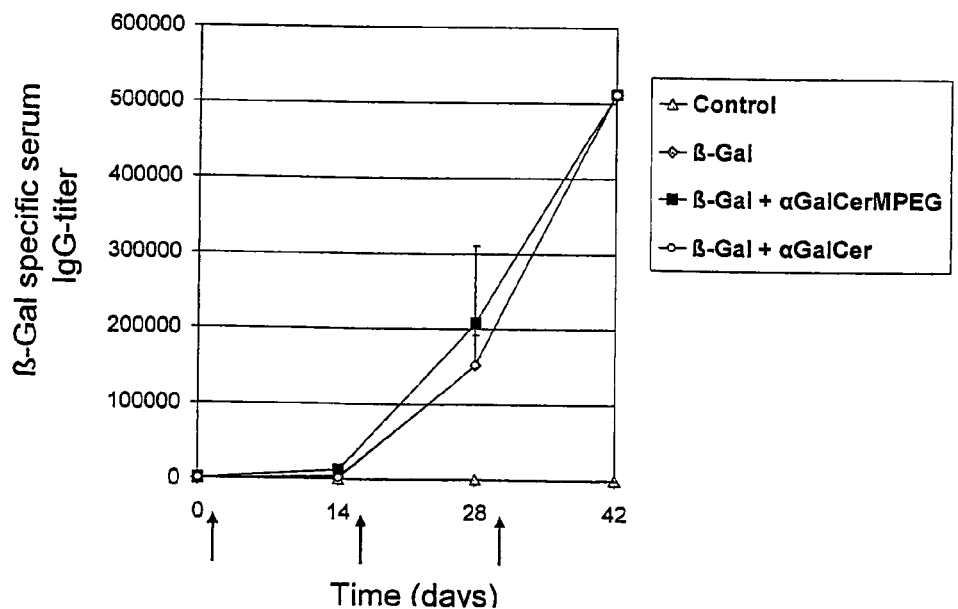

Furthermore, as can be seen from FIG. 3A and FIG. 3B, the induction of a strong IgG immune response is independent from the route of administration. A significant adjuvanticity was also observed when alphaGalCerMPEG was administered by the s.c. route (FIG. 3B).

4. Intranasal Co-administration of alphaGalCerMPEG with a Soluble Antigen Stimulate Efficient Mucosal Antibody Responses Experimental protocol: at day 38, mice were sacrificed and the final sampling was performed. Nasal, vaginal and lung lavages were obtained by flushing the organs with 1 ml of PBS supplemented with 50 mM EDTA, 0.1% BSA, and 10 mM PMSF. Lavages were then centrifuged to remove debris (10 min at 3000×g), and supernatant fluids were stored at −20° C. To determine the concentration of total IgA present in the lung and vaginal lavages, serial dilutions of the corresponding samples were incubated in microtiter plates that were previously coated with goat anti-mouse IgA (Sigma Chemie), as capture antibodies (100 μl/well). Serial dilutions of purified mouse IgA (Sigma Chemie) were used to generate a standard curve.

Figure 4A:
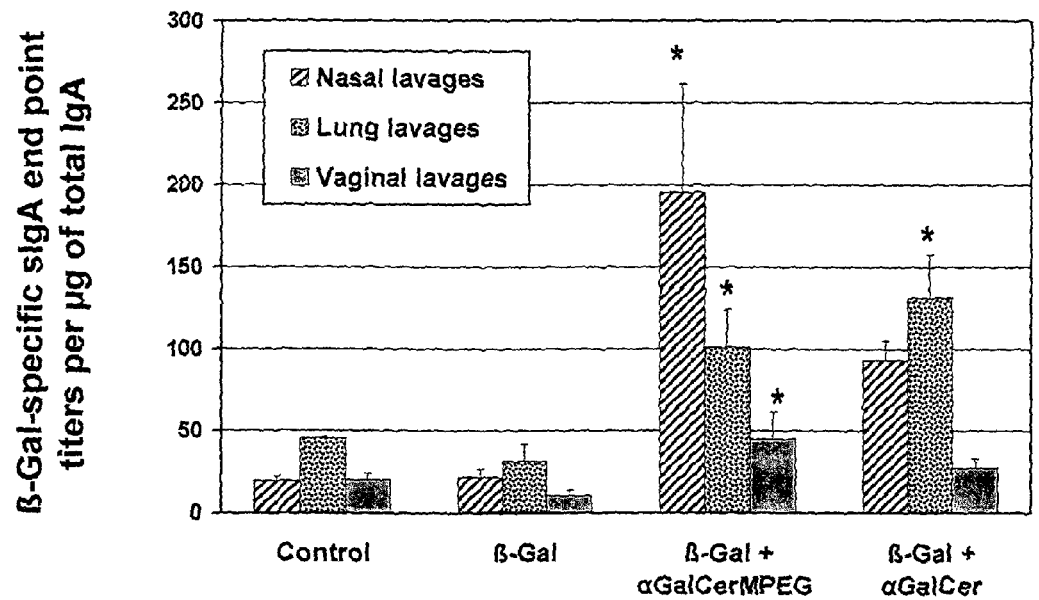
FIG. 4.
Figure 4B:
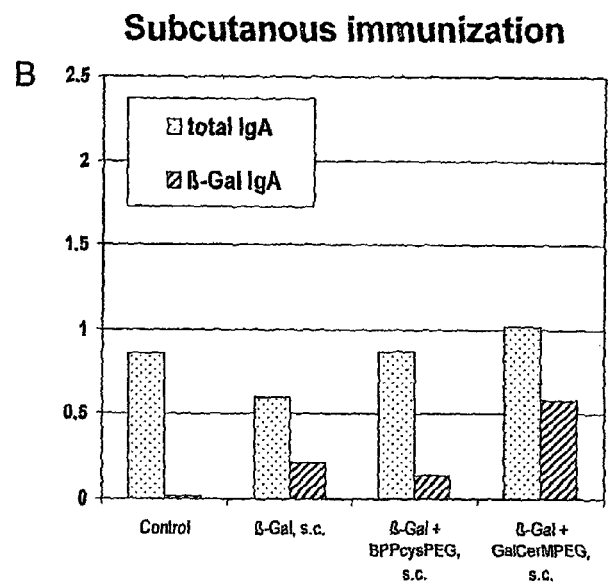

To investigate the capacity of alphaGalCerMPEG to stimulate mucosal responses against antigens co-administered by the i.n. route, the production of β-gal-specific IgA in lung was analyzed (FIG. 4) from immunized animals, immunized according to the protocol described in Example 3. While i.n. immunization with β-gal alone resulted in a weak production of detectable levels of β-gal-specific IgA in e.g. lung lavages, a significant increase in the levels of antigen-specific IgA was detected in animals immunized with β-gal and alphaGalCerMPEG (FIG. 4).

Animals vaccinated by parenteral route revealed that the co-administration of alphaGalCerMPEG results in the production of β-gal specific IgA antibodies in the lung. The levels of antigen-specific IgA significantly increased in comparison to the control (β-Gal alone) and the positive control (β-Gal co-administered with BPPcysPEG), see FIG. 4B)

5. AlphaGalCerMPEG Stimulates Efficient T Cell-mediated Proliferative Responses when Co-administered with Soluble Antigens Experimental protocol: Spleens from female BALB/c (H-2d, Harlan Winkelmann) or CD1d−/− (Jackson Laboratories) mice of 6 weeks of age were removed and pooled for analysis of cellular immune responses. Cells were grown in RPMI 1640 supplemented with 10% fetal calf serum, 100 U/ml of penicillin, 50 μg/ml of streptomycin, $5×10^{−5}$ M 2-mercaptoethanol and 1 mM L-glutamine (GIBCO BRL, Karlsruhe, Germany) and maintained at 37° C. in a humidified 5% $CO_2$ atmosphere. Spleen cell suspensions were adjusted to $5×10^6$ cells/ml in complete medium, cells were seeded with 100 μl per well in a flat-bottomed 96-well microtiter plate (Nunc) and plates were incubated for 4 days. Unstimulated spleen cells were incubated in the presence of different concentrations of the new adjuvants to analyze the in vitro stimulation capacity of alphaGalCerMPEG. T cell mediated immune responses were investigated at day 38 by measuring the proliferation of cells recovered from spleens after in vitro restimulation with β-Gal. Said spleen cells were obtained from vaccinated mice—said mice where immunized as described in Example 3—and incubated in the presence of different concentrations of the soluble β-Gal antigen. Each concentration was tested in triplicates. During the final 18 h of culture, 1 μCi of [3H]thymidine (Amersham International, Freiburg, Germany) was added to each well. Cells were then harvested on paper filters (Filtermat A; Wallac, Freiburg, Germany) by using a cell harvester (Inotech, Wohlen, Switzerland), and the amount of incorporated [3H]thymidine into the DNA of proliferating cells was determined by a β-scintillation counter (Wallac 1450, Micro-Trilux). The results are expressed as the arithmetic mean of [3H]thymidine uptake in cpm.

Figure 5:
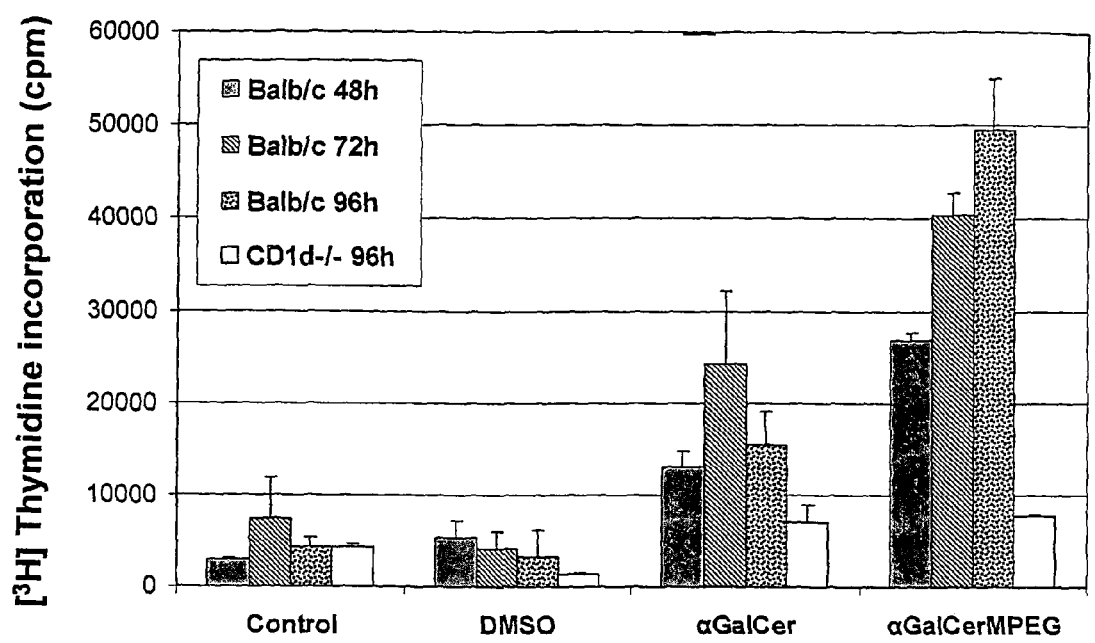
FIG. 5.

Unstimulated spleen cells incubated with different concentrations of alphaGalCerMPEG showed an increased stimulation in response to enhanced concentration of the new compound (FIG. 5) in comparison to the control. Furthermore, spleen cells incubated with different concentrations of alphaGalCer showed no dose dependent increase in the stimulation of spleen cells.

Figure 6:
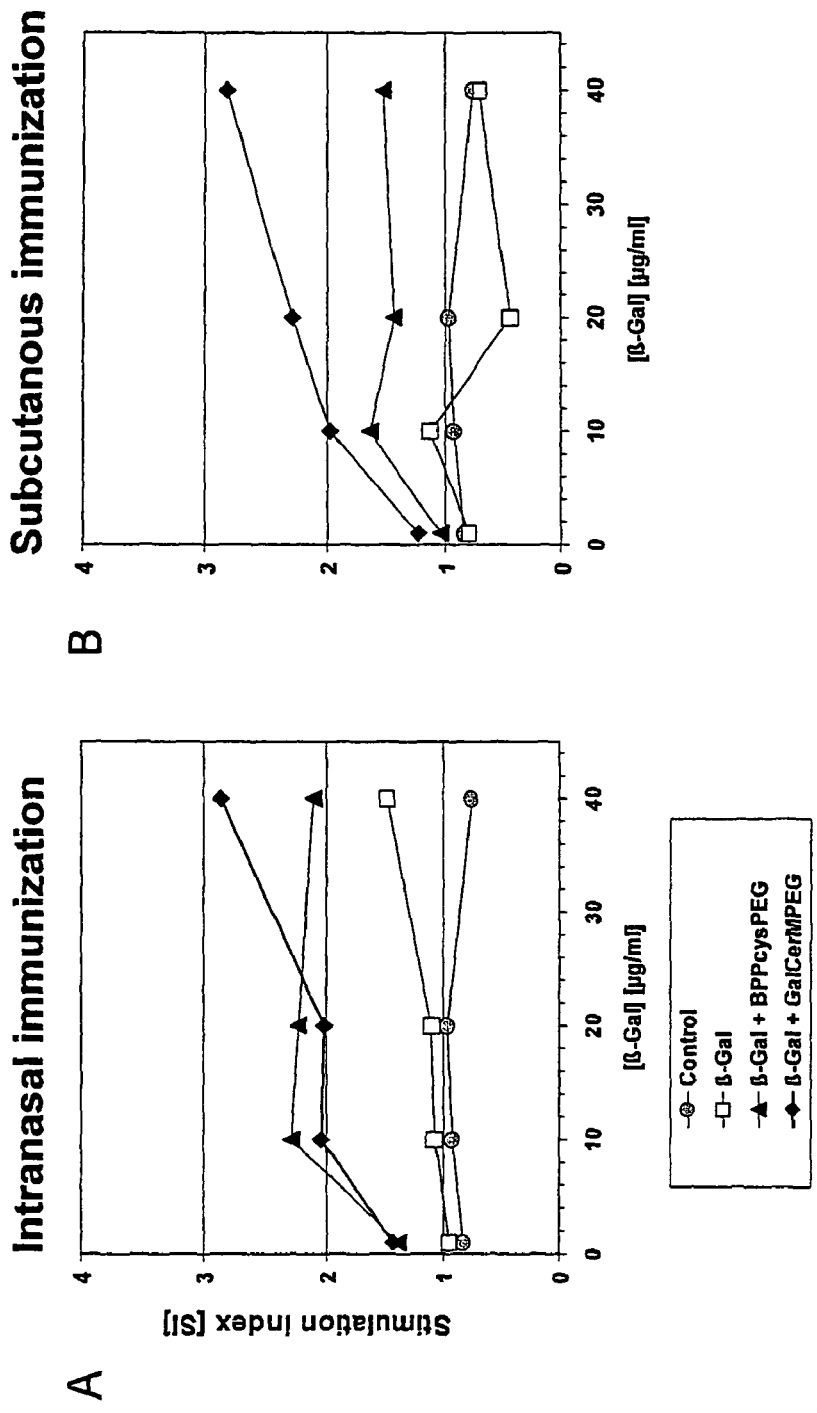
FIG. 6.

Thirty eight days following i.n. or s.c. vaccination, respectively, spleens cells were purified, re-stimulated in vitro in the presence of various amounts of β-galactosidase and their proliferative capacity was estimated by measuring the incorporation of [3H]thymidine into their DNA using a β-scintillation counter. Spleen cells from animals immunized by s.c. injection of β-gal alone, which were chosen as a control, exhibited a significant proliferative response as compared to the non immunized group (FIG. 6). A further increase in proliferation was noted in spleen cells from animals co-administrated with alphaGalCerMPEG and antigen. While i.n. administration of β-gal alone failed to induce detectable cellular proliferation, co-administration of alphaGalCerMPEG triggered the induction of an efficient proliferative response at yet low amounts of antigen (see FIG. 6).

Of note, the T cell proliferative response was observed with spleen cells of mice immunized with alphaGalCerMPEG and β-gal administered by the i.n. and the s.c. route, respectively (see FIGS. 6A and B).

In all cases a dose dependent effect was observed when increasing the concentration of β-gal in the re-stimulation experiment. Thus, the use of the new adjuvant alphaGalCerMPEG resulted in a statistically significant increment of the T cell proliferation after i.n. and s.c. administration. These results demonstrate that alphaGalCerMPEG can increase the cellular immune response.

6. Analysis of the T Helper Patterns Stimulated by Using Alpha-GalCerMPEG as Adjuvant Experimental Protocol:

Isotype ELISA: 96-well Nunc-Immuno MaxiSorp assay plates (Nunc, Roskilde, Denmark) were coated with 100 µl of β-gal (Boehringer, Mannheim, Germany) at 5 µg/ml in 0.05 M carbonate buffer (pH 9.6) per well. Serial two-fold dilutions of sera or lavages in PBS with 1% BSA and 0.05% Tween 20 were added (100 µl/well), and plates incubated for 2 h at 37° C. After washing, biotin-conjugated rat anti-mouse IgG1 or IgG2a (Pharmingen, Hamburg, Germany) were added to determine IgG subclasses. Plates were incubated for an additional 1 h at 37° C. After four washes, 100 µl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. To determine the concentration of IgG subclasses in serum, standard curves were obtained by coating the wells with an isotype-specific goat anti-mouse IgG, and then by incubating with purified mouse IgG1 or IgG2 antibodies (Dianova, Hamburg, Germany).

Figure 7A:
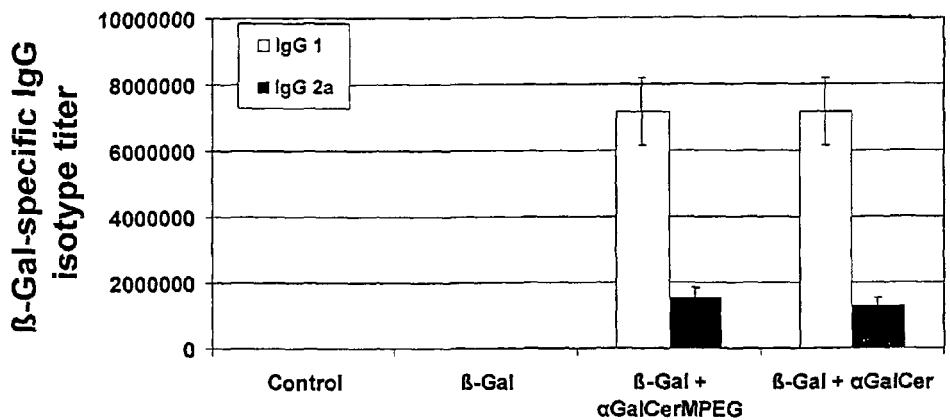
FIG. 7.
Figure 7B:
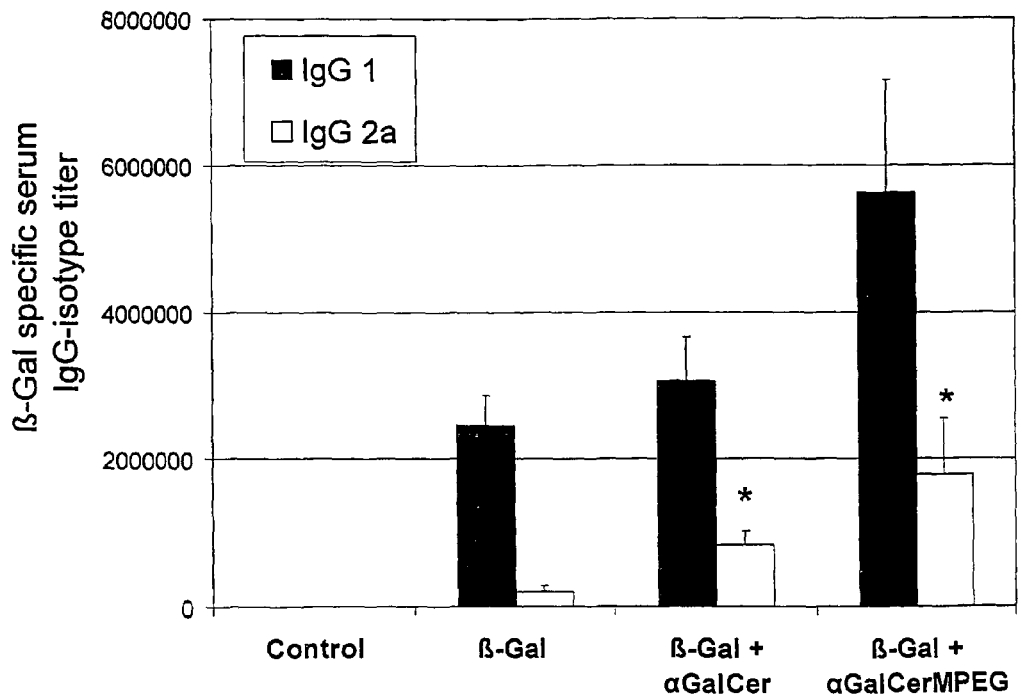

The pattern of the different subclasses of the β-gal antigen-specific IgG isotypes present in the sera of vaccinated mice is shown in FIG. 7. FIG. 7A shows the results for intranasal administration of β-Gal alone, β-Gal and alpha-GalCer and alphaGalCerMPEG. The protocol for vaccination was identical to the protocol described in Example 3. As can be ascertained from FIG. 7A, the amount of antigen specific antibodies of the IgG1 subtype (24× fold) was strongly increased after intranasal administration of the antigen using alphaGal-CerMPEG as mucosal adjuvant. Further, also in case of systemic administration, here subcutaneous administration, the expression of the IgG1 isotype is strongly (4× fold) increased, see FIG. 7B. The data represents the average titer of a group of 5 animals.

Thus, the use of alphaGalCerMPEG allows eliciting a strong antigen-specific antibody response. The triggering can be seen not only after intranasal administration but also after parenteral administration.

To characterize the type of Th response stimulated following immunization, the content of IFN-γ, IL-2, IL-6, IL-10, MCP-1, and TNFα was measured in supernatants from in vitro re-stimulated spleen cells (FIGS. 8 and 9) by the Cytometric Bead Array. Culture supernatants from proliferating cells were collected on days 2 and 4, and stored at −70° C. Determinations of IFN-γ, TNFα, IL-2, IL-6, IL-10 and MCP-1 were performed by cytometric bead array analysis using the commercial kit from BectonDickinson, according to the manufacturer's instructions. A standard curve was generated for each cytokine by using the corresponding recombinant murine cytokines (Pharmingen). Probes were incubated at room temperature for additional 2 h. The probes were analyzed subsequently by flow cytometry as described in the protocol of BD.

Figure 8:
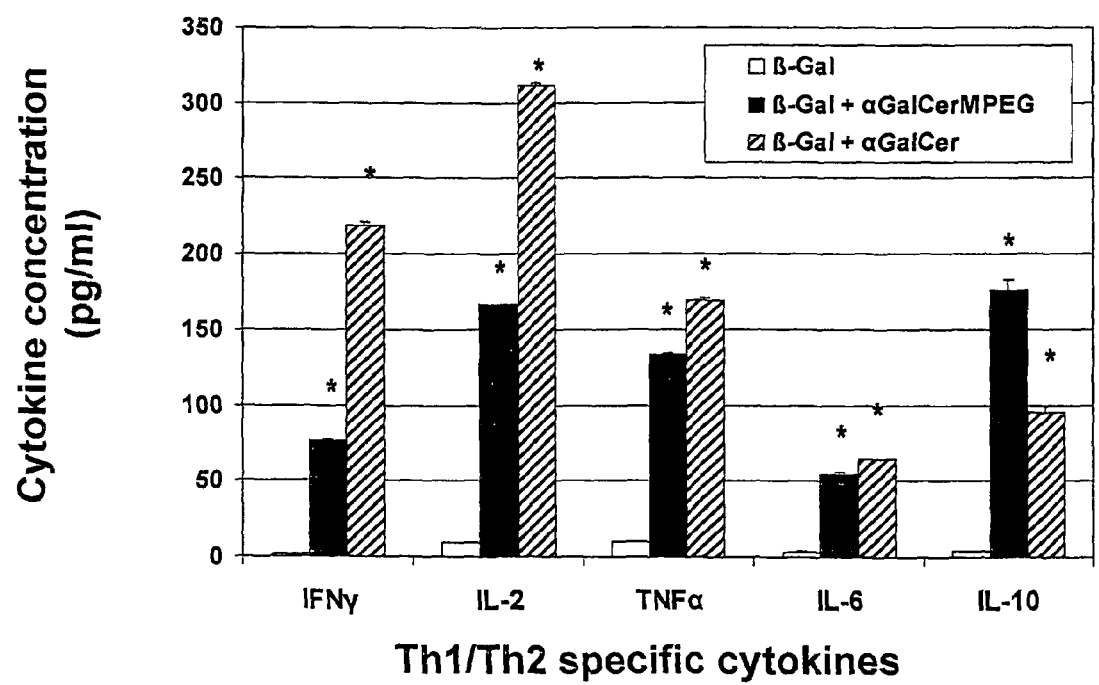
FIG. 8.

As shown in FIG. 8. IFNgamma and IL-2 were indeed secreted by spleen cells from vaccinated mice. Interestingly, the concentration of the Th1 cytokines secreted by cells recovered from mice vaccinated by the intranasal route with alphaGalCerMPEG were significantly lower than those observed in animals receiving alphaGalCer. This suggest the induction of more strongly polarized Th2 like response when the pegylated derivative of alphaGalCer was used. The secretion of the pro-inflammatory cytokines TNFalpha and IL-6 was similar using both compounds. However, significantly higher levels of the anti-inflammatory cytokine IL-10 were secreted by cells derived from mice receiving alphaGalCerMPEG. This may suggest that the pegylated derivative is pharmacologically more acceptable in comparison with the non-derivatisized compound alphaGalCer.

Figure 9:
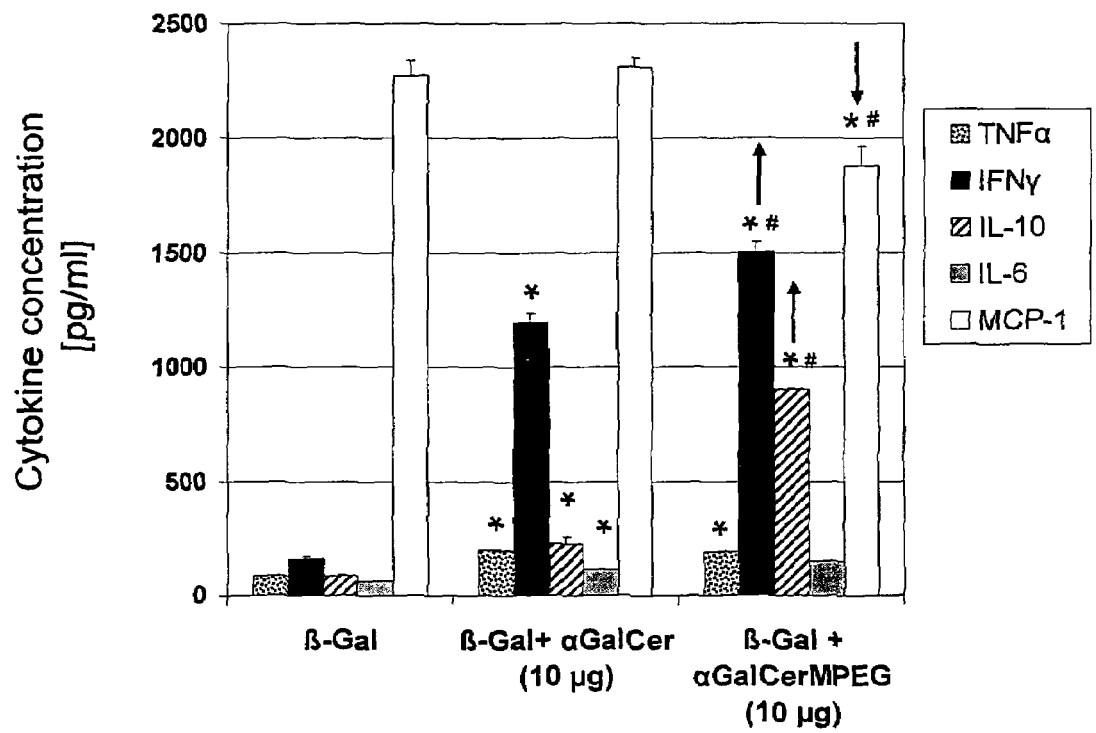
FIG. 9.

The parenteral administration (s.c.) of β-Gal with alphaGalCerMPEG or alphaGalCer demonstrates that the usage of these adjuvants unduced a significant enhanced secretion of TNFalpha, IL-10 and IFNgamma. In contrast to animals vaccinated with the parenteral alphaGalCer derivative, mice vaccinated with beta-Gal co-administered with alphaGalCerMPEG showed significantly higher levels of IL-10 and IFNgamma and a decrease in the secretion of MCP-1, as shown in FIG. 9. This suggests that the pegylated derivative is pharmacologically more active in comparison with the non-derivatisized compound alphaGalCer.

7. Analysis of the T Helper Patterns Stimulated by Using AlphaGalCerMPEG as Adjuvant by Elispot Experimental protocol: Spleens from vaccinated mice were removed and pooled for analysis of cellular immune responses. The protocol for vaccination was identical to the protocol described in Example 3. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Lymph node and spleen cell suspensions were adjusted to $5 \times 10^6$ cells/ml in complete medium, cells were seeded with 100 µl per well in a flat-bottomed 96-well microtiter plate (Nunc) and plates were incubated 24 h (IFN-gamma) or 48 h (IL-2 and IL-4) in the absence or presence of a beta-Gal peptide (TPHARIGL) encompassing a MHC class I-restricted epitope (for IFNgamma) or the beta-Gal protein (for IL-2 and IL-4), at a concentration of 10 μM. Then, cells were removed and the plates processed according to manufacture's instructions. Colored spots were counted with a C.T.L. Elispot reader and analysed using the ImmunoSpot image analyzer software v3.2.

Figure 10:
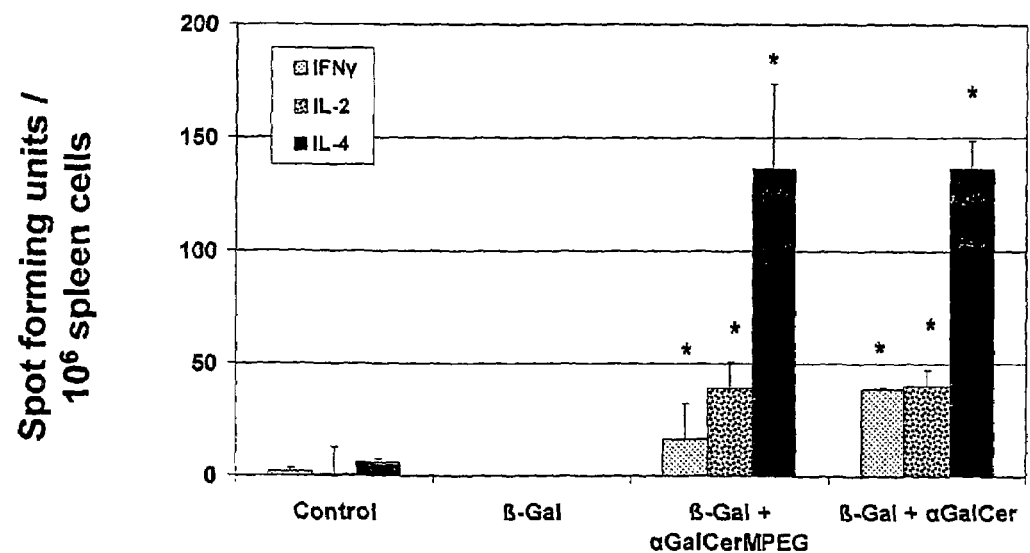
FIG. 10.
Figure 10:
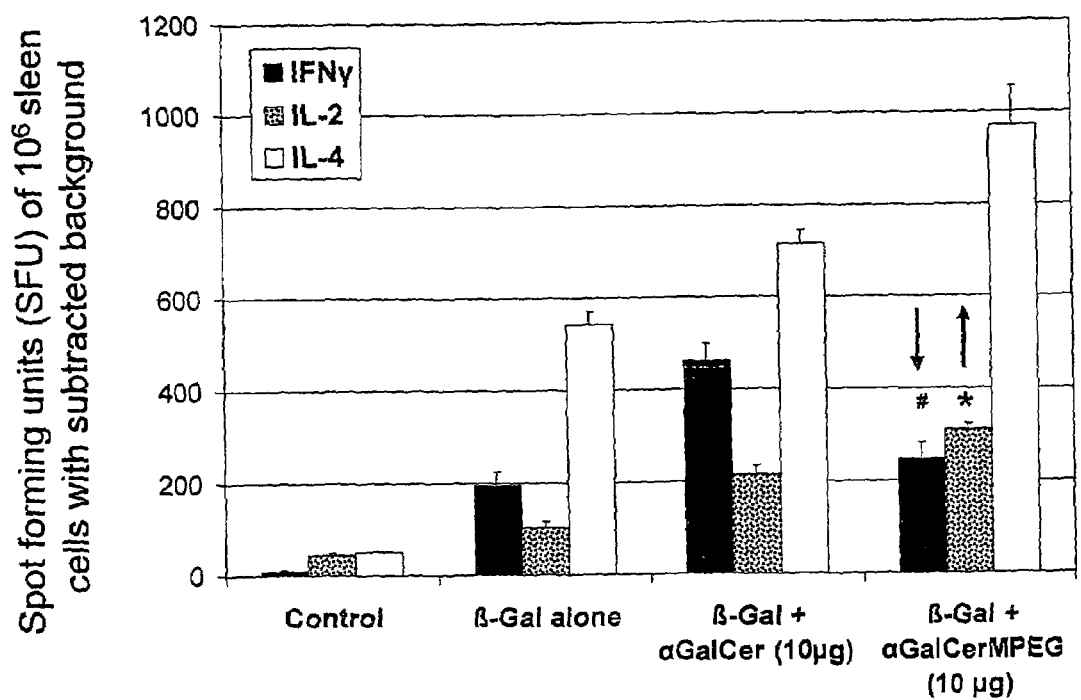

Thus, to further characterize the T helper responses, the number of beta-Gal specific IFNgamma, IL-2 and IL-4 secreting cells present in spleens of vaccinated mice was determined. In agreement with the above results for IgG isotypes, high numbers of IL-4 secreting cells were detected in mice receiving alphaGalCerMPEG or alphaGalCer (FIG. 10). In contrast, the number of IFNgamma and IL-2 secreting cells was increased to a significant minor extent in response to stimulation with MHC class I restricted peptide and the β-Gal protein, respectively.

8. Analysis of the Stimulation of Murine NK and NKT Cells by Using AlphaGalCerMPEG as Adjuvant Experimental protocol: Mice received 10 μg of alphaGalCer or alphaGalCerMPEG by s.c. route, whereas control animals were injected by intraperitoneal route with 100 μg of CpG. After 2 days, they were sacrified and their splenocytes were used as effector cells in a standard 51Cr-release assay using YAC-1 cells as targets for NK cells. Effector cells were washed and their concentration was adjusted to $1\times10^6$/ml. In parallel, target cells were incubated in RPMKI medium without FCS containing 100 μCi of 51Cr for 2 h. Then, target cells were extensively washed with RPMI medium containing FCS and co-incubated in triplicates with effector cells at different effector:target (E:T) ratios. After 4 h, cells were centrifuged and the radioactivity present in supernatants was measured by scintillation counting. Maximal lysis was determined after lysis with 5% Tween X-100, whereas spontaneous lysis was measured in supernatants of untreated target cells. Results are expressed as percentage of lysed cells, accordingly to the formula: (sample−spontaneous lysis)/(maximal lysis−spontaneous lysis)×100.

Figure 11:
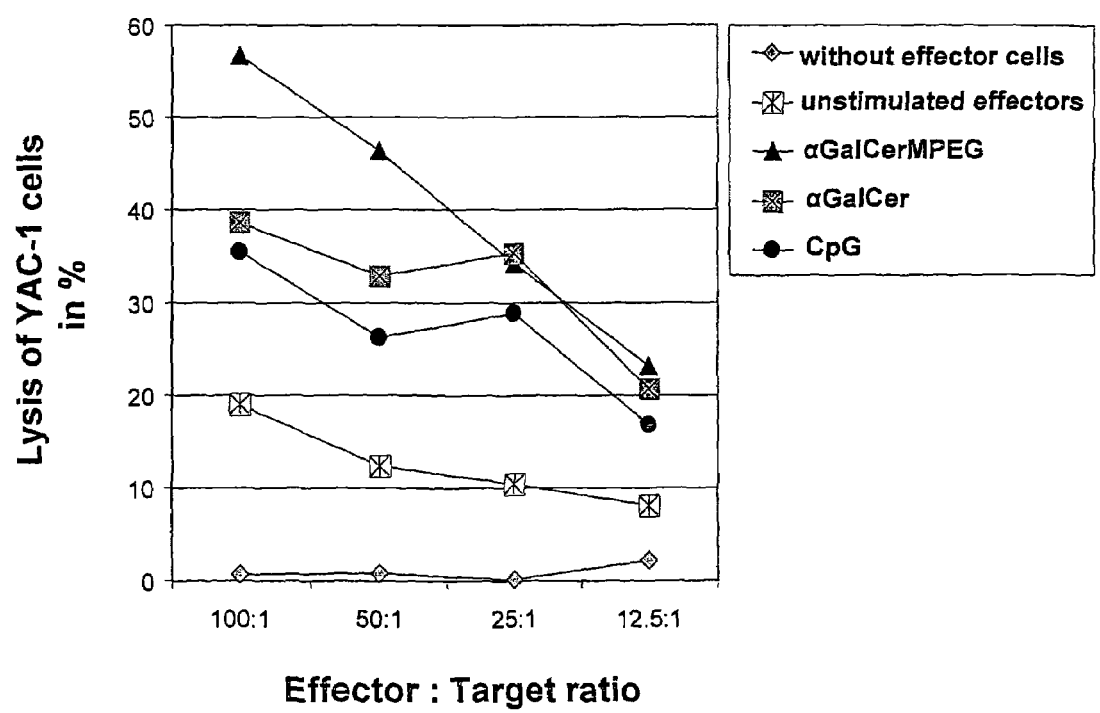
FIG. 11.

To analyze the in vivo influence of αGalCerMPEG on the cytotoxic activity of NK cells, mice were injected with different adjuvants, i.e. αGalCer, αGalCerMPEG and CpG. After 2 days, splenocytes were used as effector cells in a 51Cr-release assay with YAC-1 cells, a well-known target for NK cells. After in vivo stimulation using the hydrophobic αGalCer (10 μg) or the adjuvant CpG, a similar cytotoxic potential of splenocytes against the tumor cell line YAC-1 was observed (37-36% and 34-27% at effector: target ratios of 100:1 and 50:1 respectively). On the other hand, when αGalCerMPEG was used (i.e., 10 μg which correspond to 1 μg αGalCer), spleen cells mediated the lysis of 56 and 46% of YAC-1 cells at an effector to target ratio of 100:1 and 50:1, respectively (FIG. 11). Cytotoxicity was also assessed on fluorescence-labeled syngeneic spleen cell populations administered by i.v. injection into groups of mice.

Figure 12:
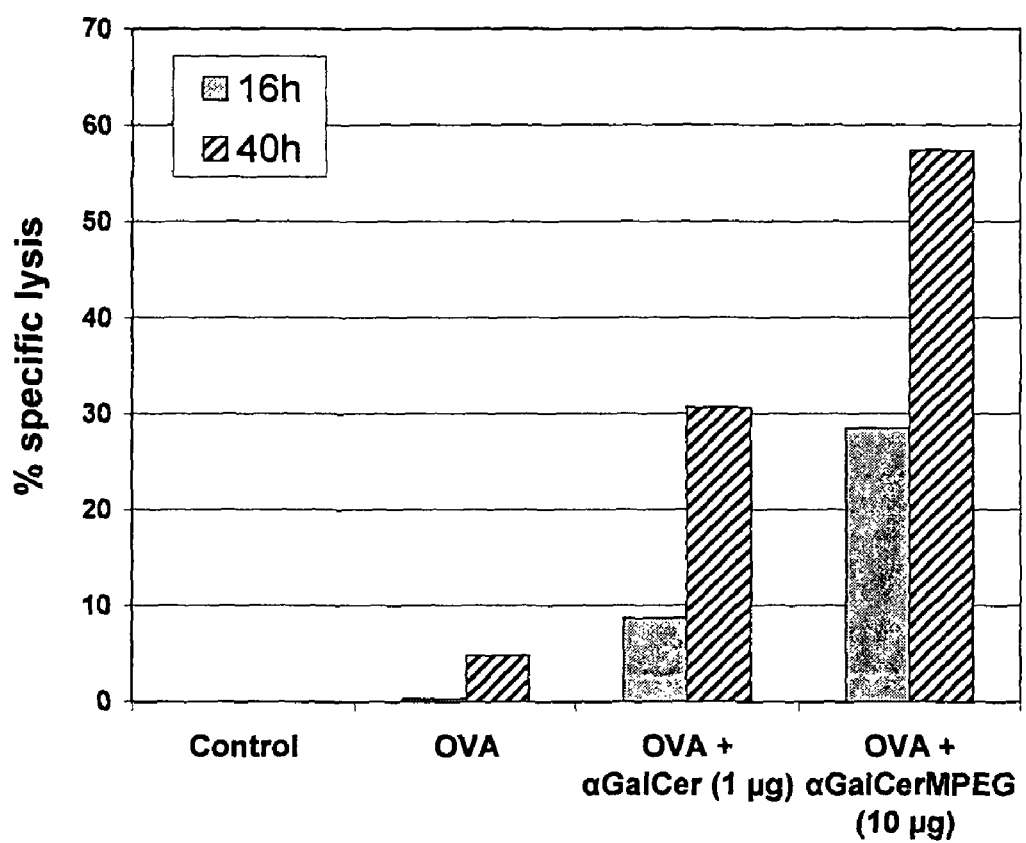
FIG. 12.

9. Analysis of the Cytolytic Activity of Cytotoxic T Cells by Using AlphaGalCerMPEG as Adjuvant Experimental protocol: Six to eight weeks-old female C57Bl6 mice were purchased from Harlan Winkelmann GmbH (Borchen, Germany) and treated in accordance with local and European Community guidelines. Groups of 5 mice each were immunized on day 1, 14 and 28 with 50 μg Ovalbumin (Sigma, Germany) alone or with 10 μg alphaGalCerMPEG or alphaGalCer. For intranasal immunization, 10 μl were applied to each naris, whereas for the s.c. injection Ovalbumin (ova) with or without alphaGalCerMPEG or alphaGalCer was resuspended in a volume of 50 μl PBS per animal. The determination of the in vivo lymphocyte-mediated cytotoxicity followed a protocol described by Hermans et. Al. (Herman, I. F., et. Al., 2004, The vital assay, J Immunol Methods, 285, 25-40). A suspension of splenocytes from naïve mice was depleted of red cells and split into two equal portions. The target cell preparation was labelled with a high concentration (1 μM) of CFSE (Molecular Probes) and pulsed for 1 h at 37° C. with the dominant OVA peptide (aa 257-264) at a concentration of 15 μg/ml. The control population was labelled with a low concentration (0.1 μM) of CFSE and further incubated for 1 h at 37° C. without peptide. Equal numbers of each cell population were mixed. A total amount of $2\times10^7$ cells was adoptively transferred by intraveneous injection into the immunized mice. Cells from spleens were analyzed by flow cytometry after 16 h and 40 h, with the FACScalibur using the software BD cell Quest Pro. Specific lysis was distinguished by the loss of the peptide-pulsed CFSEhi population in comparison with the control CFSElo population. The following formula was used to calculate the percentage of specific lysis: 100−([(% CFSEhi in immunized mize/% CFSElo immunized mize)/(% CFSEhi in control mize/% CFSElo in control mice)]×100). Cytotoxic activity was assessed with any variability in the proportion of cells in the different target populations assessed in a non-immunized control group for CTL assays. As shown in FIG. 12, with hydrophobic alphaGalCer (10 μg), a 6.4 fold (30%) increase of the cytotoxic potential of splenocytes with respect to splenocytes recovered from animals receiving the OVA antigen alone (5%) was observed. However, when alphaGalCerMPEG was used (i.e. 10 μg which correspond to 1 μg alphaGalCer) spleen cells mediated the lysis of nearly 60& of peptide-coated target cells and showed a 12 fold increase of the cytotoxic potential with respect to splenocytes recovered from animals receiving the antigen alone (5%).

The invention claimed is:

1. An alpha-Hexosylceramide (alpha-HexCer) conjugate according to formula (I)

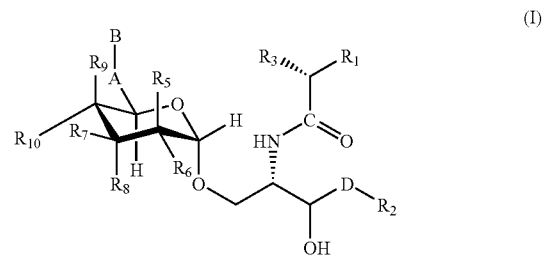

wherein
A is $CH_2$ or CO;
B represents $R_4$, $OR_4$, $NHR_4$, $PO_3R_4$, or $SO_3R_4$
where $R_4$ is a conjugate moiety which is a water-soluble and physiologically tolerated polymer;
$R_1$ and $R_2$ can be identical or different and are independently a linear or branched $C_{10}$-$C_{30}$ alkyl- and/or alkenyl-groups;
D represents $CH_2$ or CH(OH);
$R_3$ represents hydrogen or OH;
$R_5$ and $R_6$ are substituents where either $R_5$ represents hydrogen and $R_6$ represents hydrogen, OH, $OC_1$-$C_6$ alkyl, NH2, $NHCOC_1$-$C_6$ alkyl or $R_6$ is hydrogen and $R_5$ represents hydrogen, OH, $OC_1$-$C_6$ alkyl, $NH_2$, $NHCOC_1$-$C_6$ alkyl;
$R_7$ and $R_8$ are substituents where either $R_7$ represents hydrogen and $R_8$ represents hydrogen, OH, $OC_1$-$C_6$ alkyl, $NH_2$, $NHCOC_1$-$C_6$ alkyl or $R_8$ is hydrogen and $R_7$ represents hydrogen, OH, $OC_1$-$C_6$ alkyl, $NH_2$, $NHCOC_1$-$C_6$ alkyl;

$R_9$ and $R_{10}$ are substituents where either $R_9$ represents hydrogen and $R_{10}$ represents hydrogen, OH, $OC_1$-$C_6$ alkyl, $NH_2$, $NHCOC_1$-$C_6$ alkyl or $R_{10}$ is hydrogen and $R_9$ represents hydrogen, OH, $OC_1$-$C_6$ alkyl, $NH_2$, $NHCOC_1$-$C_6$alkyl; or salts or solvates thereof.

2. The alpha-HexCer conjugate according to claim 1 characterized in that $R_4$ contains at least one polyalkylene glycol unit of the formula:

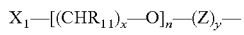

where
$X_1$ is hydrogen or a hydrocarbon which may contain heteroatom(s);
Z is a divalent linkage group, such as C=O or $CHR_{11}$;
$R_{11}$ is independently any one of hydrogen, OH, $OR_{12}$ or CO—$R_{13}$;
$R_{12}$ is independently any one of hydrogen or $C_1$-$C_6$ alkyl group;
$R_{13}$ is independently any one of hydrogen, OH, $OR_{12}$ or $NR_{14}R_{15}$;
$R_{14}$ and $R_{15}$ are independently any one of hydrogen or hydrocarbon which may contain heteroatom(s) and which may form a ring;
n is an integer of 1 to 100;
x is independently an integer of 1 to 10;
y is an integer of 0 to 10.

3. The alpha-HexCer conjugate according to claim 1 characterized in that $R_4$ comprises at least two chains having polyalkylene glycol units.

4. The alpha-Hexcer conjugate according to claim 2, characterized in that the polyalkylene glycol units are polyethylene units, polypropylene units and/or polybutylene units.

5. The alpha-HexCer conjugate according to claim 1 characterized in that R4 is methoxypolyethylenglycol-carbonyl residue.

6. The alpha-HexCer conjugate according to claim 1 characterized in that $R_4$ is (S)-10-Amino-6,9,13,16-tetraoxo-N,N',8,14-tetrakis(3,6,9,12-tetraoxamidec-1-yl)-5,8,14,17-tetraazahenicosane-1,21-diamide, 7. The alpha-HexCer conjugate according to claim 1, characterized in that $R_1$ is a $C_{19}$-$C_{29}$ alkyl group and $R_3$ is hydrogen.

8. The alpha-HexCer conjugate according to claim 1, characterized in that $R_2$ is a $C_{10}$-$C_{20}$ alkyl group.

9. The alpha-HexCer conjugate according to claim 1, characterized in that each of $R_6$, $R_7$ and $R_9$ is a hydroxyl group.

10. The alpha-HexCer conjugate according to claim 1, wherein $R_1$ is a $C_{24}$ alkyl group, $R_2$ is a $C_{14}$ alkyl group, $R_3$ is hydrogen and each of $R_6$, $R_7$ and $R_9$ is a hydroxyl group.

11. A pharmaceutical composition comprising an alpha-HexCer conjugate according to formula (I)

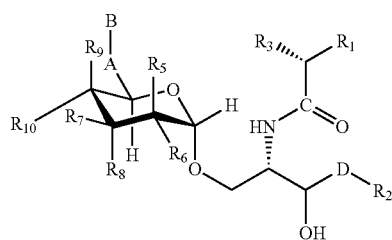

wherein
A is $CH_2$ or CO;
B represents $R_4$, $OR_4$, $NHR_4$, $PO_3R_4$, or $SO_3R_4$ where $R_4$ is a conjugate moiety which is a water-soluble and physiologically tolerated polymer;
$R_1$ and $R_2$ can be identical or different and are independently a linear or branched $C_{10}$-$C_{30}$ alkyl- and/or alkenyl-groups;
D represents $CH_2$ or CH(OH);
$R_3$ represents hydrogen or OH;
$R_5$ and $R_6$ are substituents where either $R_5$ represents hydrogen and $R_6$ represents hydrogen, OH, $OC_1$-$C_6$ alkyl, NH2, $NHCOC_1$-$C_6$ alkyl or $R_6$ is hydrogen and $R_5$ represents hydrogen, OH, $OC_1$-$C_6$ alkyl, $NH_2$, $NHCOC_1$-$C_6$ alkyl;
$R_7$ and $R_8$ are substituents where either $R_7$ represents hydrogen and $R_8$ represents hydrogen, OH, $OC_1$-$C_6$ alkyl, $NH_2$, $NHCOC_1$-$C_6$ alkyl or $R_8$ is hydrogen and $R_7$ represents hydrogen, OH, $OC_1$-$C_6$ alkyl, $NH_2$, $NHCOC_1$-$C_6$ alkyl;
$R_9$ and $R_{10}$ are substituents where either $R_9$ represents hydrogen and $R_{10}$ represents hydrogen, OH, $OC_1C_6$ alkyl, $NH_2$, $NHCOC_1$-$C_6$ alkyl or $R_{10}$ is hydrogen and $R_9$ represents hydrogen, OH, $OC_1$-$C_6$ alkyl, $NH_2$, $NHCOC_1$-$C_6$alkyl; or salts or solvates thereof and a pharmaceutically acceptable carrier, diluent, preservative, adjuvants, immunomodulators and/or excipient.

12. A pharmaceutical composition comprising:
an alpha-HexCer conjugate according to claim 1 as an adjuvant,
a pharmaceutically active ingredient, and
a pharmaceutically acceptable carrier, diluent, preservative, adjuvants other than the alpha-HexCer conjugate defined in claim 1, immunomodulators or excipient.

13. The pharmaceutical composition according to claim 12, characterized in that the pharmaceutical composition is a vaccine.

14. The pharmaceutical composition according to claim 12, wherein the pharmaceutical active ingredient(s) comprises at least one or more different antigens in the form of peptides, proteins, polysaccharides, glycolipids or DNA encoding said peptides, proteins, polysaccharides and glycolipids or antigen delivery systems which provide said peptides, proteins, polysaccharides and glycolipids.

15. The pharmaceutical composition according to claim 14, characterized in that the pharmaceutically active agent is selected from tumor antigen(s) and antigen(s) derived from infectious agents.

16. The pharmaceutical composition according to claim 12, further comprising one or more anti-inflammatory molecules, anti-angiogenic molecules, cytotoxic molecules, immunomodulatory molecules, or antibodies or mixtures thereof.

17. A pharmaceutical composition according to claim 12, characterized in that the pharmaceutically active ingredient and/or alpha-HexCer conjugate are associated and/or incorporated and/or coated to a physical particle or biological particle.

18. A pharmaceutical composition according to claim 12 provided in a formulation suitable for mucosal administration.

19. A pharmaceutical composition according to claim 12 provided in a formulation suitable for parenteral administration.

20. A systemic or mucosal adjuvant comprising an alpha-Hexosylceramide (alpha-HexCer) conjugate according to formula (I)

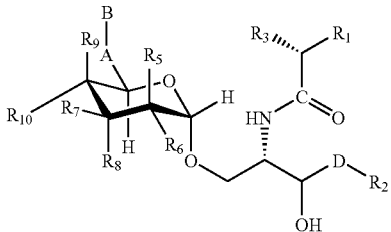 (I)

wherein
- A is $CH_2$ or CO;
- B represents $R_4$, $OR_4$, $NHR_4$, $PO_3R_4$, or $SO_3R_4$ where $R_4$ is a conjugate moiety which is a water-soluble and physiologically tolerated polymer;
  - $R_1$ and $R_2$ can be identical or different and are independently a linear or branched $C_{10}$-$C_{30}$ alkyl- and/or alkenyl-groups;
- D represents $CH_2$ or CH(OH);
- $R_3$ represents hydrogen or OH;
- $R_5$ and $R_6$ are substituents where either $R_5$ represents hydrogen and $R_6$ represents hydrogen, OH, $OC_1$-$C_6$ alkyl, NH2, $NHCOC_1$-$C_6$ alkyl or $R_6$ is hydrogen and $R_5$ represents hydrogen, OH, $OC_1$-$C_6$ alkyl, $NH_2$, $NHCOC_1$-$C_6$ alkyl;
- $R_7$ and $R_8$ are substituents where either $R_7$ represents hydrogen and $R_8$ represents hydrogen, OH, $OC_1$-$C_6$ alkyl, $NH_2$, $NHCOC_1$-$C_6$ alkyl or $R_8$ is hydrogen and $R_7$ represents hydrogen, OH, $OC_1$-$C_6$ alkyl, $NH_2$, $NHCOC_1$-$C_6$ alkyl;
- $R_9$ and $R_{10}$ are substituents where either $R_9$ represents hydrogen and $R_{10}$ represents hydrogen, OH, $OC_1$-$C_6$ alkyl, $NH_2$, $NHCOC_1$-$C_6$ alkyl or $R_{10}$ is hydrogen and $R_9$ represents hydrogen, OH, $OC_1$-$C_6$ alkyl, $NH_2$, $NHCOC_1$-$C_6$alkyl; or salts or solvates thereof.

21. The systemic or mucosal adjuvant of claim 20 formulated for parenteral administration.

22. A kit comprising the hexosylceramide conjugate according to claim 1.

23. The pharmaceutical composition of claim 14 wherein said antigen delivery systems are selected from the group consisting of virosomes, physical particles, and attenuated vaccines.

24. The pharmaceutical composition of claim 23 wherein said physical particle are selected from the group consisting of microparticles, nanoparticles, liposomes, ISCOM, copolymers, and biological particles.

25. The pharmaceutical composition of claim 24 wherein said biological particle are selected from the group consisting of bacterial ghosts, virus-like particles (VLP), and particle like viruses (PLVs).

26. The pharmaceutical composition of claim 16 wherein said immunomodulatory molecules are selected from the group consisting of chemokines, cytokines, CD40 ligand, and costimulatory molecules.

27. The pharmaceutical composition of claim 17 wherein said physical particle is selected from the group consisting of microparticles, nanoparticles, liposomes, ISCOM, copolymers, and wherein said biological particle is selected from the group consisting of bacterial ghosts, virosomes, and virus-like particles.

* * * * *

UNITED STATES PATENT AND TRADEMARK OFFICE
CERTIFICATE OF CORRECTION

| | | |
|---|---|---|
| PATENT NO. | : 8,053,417 B2 | Page 1 of 1 |
| APPLICATION NO. | : 12/090279 | |
| DATED | : November 8, 2011 | |
| INVENTOR(S) | : Thomas Ebensen | |

It is certified that error appears in the above-identified patent and that said Letters Patent is hereby corrected as shown below:

On the title page, correct the spelling of city of the Assignee to Braunschweig.

Signed and Sealed this
Twentieth Day of December, 2011

David J. Kappos
*Director of the United States Patent and Trademark Office*